(12) United States Patent
Dai et al.

(10) Patent No.: US 8,983,812 B2
(45) Date of Patent: *Mar. 17, 2015

(54) SYSTEMS AND METHODS FOR WAVEFRONT ANALYSIS OVER CIRCULAR AND NONCIRCULAR PUPILS

(71) Applicant: AMO Development, LLC, Santa Clara, CA (US)

(72) Inventors: Guang-ming Dai, Fremont, CA (US); Virendra N. Mahajan, Rancho Palos Verdes, CA (US)

(73) Assignee: AMO Development, LLC, Santa Ana, CA (US)

( * ) Notice: Subject to any disclaimer, the term of this patent is extended or adjusted under 35 U.S.C. 154(b) by 98 days.

This patent is subject to a terminal disclaimer.

(21) Appl. No.: 13/871,143

(22) Filed: Apr. 26, 2013

(65) Prior Publication Data

US 2013/0246493 A1    Sep. 19, 2013

Related U.S. Application Data

(63) Continuation of application No. 11/775,412, filed on Jul. 10, 2007, now Pat. No. 8,504,329.

(60) Provisional application No. 60/819,587, filed on Jul. 10, 2006.

(51) Int. Cl.
*G06F 7/60*    (2006.01)
*G01B 11/02*    (2006.01)
*A61B 3/10*    (2006.01)
(Continued)

(52) U.S. Cl.
CPC ............ *G06F 7/548* (2013.01); *A61B 3/107* (2013.01); *A61B 3/1015* (2013.01); *G06F 17/10* (2013.01); *A61F 2009/0088* (2013.01); *A61B 3/103* (2013.01); *A61F 9/008* (2013.01); *A61F 9/00806* (2013.01); *A61F 9/00812* (2013.01); *A61F 2009/00848* (2013.01)
USPC ................ 703/2; 356/512; 351/212; 351/222

(58) Field of Classification Search
CPC ........ A61B 3/1015; A61B 3/107; A61B 3/11; A61F 2009/0088; A61F 9/00806; G06F 17/10; G06F 19/3437
See application file for complete search history.

(56) References Cited

U.S. PATENT DOCUMENTS 5,121,337 A    6/1992    Brown
5,287,273 A    2/1994    Kupfer et al.
(Continued)

OTHER PUBLICATIONS

Dai, Guang-ming, et al., "Non recursive determination of orthonormal polynomials with matrix formulation." *Optics Letters*, The Optical Society of America, vol. 32, No. 1, (2007): pp. 74-76.
(Continued)

*Primary Examiner* — Akash Saxena
(74) *Attorney, Agent, or Firm* — AMO Development, LLC

(57) ABSTRACT

Systems, methods, and software for determining a set of analytical or numerical polynomials that is orthonormal over circular or noncircular pupils are described. Closed-form orthonormal polynomials for circular, annular, hexagonal, elliptical, rectangular, and square pupils are derived. Such techniques can be applied to ray tracing as in the optical design and wavefront fitting from measurement as in the optical testing. These approaches can also be applied to wavefront reconstruction in adaptive optics.

21 Claims, 17 Drawing Sheets

(51) Int. Cl.

| | | |
|---|---|---|
| *G06F 7/548* | (2006.01) | |
| *A61B 3/103* | (2006.01) | |
| *A61B 3/107* | (2006.01) | |
| *G06F 17/10* | (2006.01) | |
| *A61F 9/008* | (2006.01) | |

(56) References Cited

U.S. PATENT DOCUMENTS

| | | | | |
|---|---|---|---|---|
| 5,446,681 | A | | 8/1995 | Gethner et al. |
| 6,002,484 | A | * | 12/1999 | Rozema et al. ............... 356/515 |
| 6,556,961 | B1 | | 4/2003 | Lafe |
| 7,088,457 | B1 | | 8/2006 | Zou et al. |
| 7,311,400 | B2 | | 12/2007 | Wakil et al. |
| 7,553,022 | B2 | | 6/2009 | Neal et al. |
| 7,796,784 | B2 | | 9/2010 | Kondo et al. |
| 8,452,574 | B2 | * | 5/2013 | Wilcox et al. ..................... 703/2 |
| 8,504,329 | B2 | * | 8/2013 | Dai et al. ........................... 703/2 |
| 2001/0016695 | A1 | | 8/2001 | Mihashi et al. |
| 2002/0186346 | A1 | | 12/2002 | Stantz et al. |
| 2003/0086063 | A1 | | 5/2003 | Williams et al. |
| 2003/0184736 | A1 | | 10/2003 | Fukuhara et al. |
| 2003/0194144 | A1 | | 10/2003 | Wenzel et al. |
| 2003/0206289 | A1 | | 11/2003 | Matsuyama |
| 2004/0130705 | A1 | | 7/2004 | Topa |
| 2005/0012898 | A1 | | 1/2005 | Chernyak et al. |
| 2005/0057723 | A1 | | 3/2005 | Wakil et al. |
| 2005/0152583 | A1 | | 7/2005 | Kondo et al. |
| 2005/0288910 | A1 | | 12/2005 | Schlessinger et al. |
| 2007/0165242 | A1 | | 7/2007 | Scott et al. |
| 2008/0077644 | A1 | * | 3/2008 | Dai et al. ...................... 708/401 |
| 2008/0086520 | A1 | | 4/2008 | Epelbaum |
| 2009/0036980 | A1 | | 2/2009 | Norrby et al. |
| 2009/0284753 | A1 | | 11/2009 | Neal et al. |
| 2010/0114076 | A1 | | 5/2010 | Reinstein et al. |
| 2010/0192709 | A1 | | 8/2010 | Wilcox et al. |
| 2010/0299113 | A1 | | 11/2010 | Robinson et al. |
| 2011/0027723 | A1 | | 2/2011 | Suzuki et al. |
| 2011/0149241 | A1 | | 6/2011 | Dai |
| 2011/0178785 | A1 | | 7/2011 | Tinnemans et al. |
| 2012/0206719 | A1 | | 8/2012 | Tanaka |
| 2013/0018640 | A1 | * | 1/2013 | Etgen et al. ......................... 703/2 |
| 2013/0158840 | A1 | * | 6/2013 | Lu et al. ......................... 701/104 |
| 2013/0246493 | A1 | * | 9/2013 | Dai et al. ........................ 708/441 |
| 2014/0036180 | A1 | * | 2/2014 | Takiguchi et al. ............... 349/33 |

OTHER PUBLICATIONS

Dunkl, C., "Orthogonal Polynomials on the Hexagon." *Society for Industrial and Applied Mathematics*, vol. 47, No. 2, (1987): pp. 343-351.

Mahajan, V., 'Zernike annular polynomials for imaging systems with annular pupils,' *The Journal of The Optical Society of America*, vol. 71, No. 1, (1981): pp. 75-85.

Mahajan, V., "Zernike annular polynomials for imaging systems with annular pupils." *The Journal of the Optical Society of America*, vol. 1, No. 6, (1984): p. 685.

Mahajan, V. N., "Zernike Annular Polynomials and Optical Aberrations of Systems with Annular Pupils." *Supplement to Optics & Photonics News*, vol. 5, No. 11, (Nov. 11, 1994): pp. 8126-8127.

Mahajan, V. N., et al., "Orthonormal polynomials for hexagonal pupils." *Optics Letters*, The Optical Society of America, vol. 31, No. 16, (2006): pp. 2462-2464.

Mahajan, V. N., et al., "Orthonormal polynomials in wavefront analysis: analytical solution." *The Journal of the Optical Society of America*, vol. 24, No. 9, (Sep., 2007): pp. 2994-3016.

Van Barel, M., et al., "Orthogonal Polynomial Vectors and Least Square Approximation for Discrete Inner Product." *Electronic Transactions on Numerical Analysis*, vol. 3, (1995): pp. 1-23.

PCT Patent Application No. PCT/US2007/073075, filed Jul. 9, 2007, 59 pages.

PCT International Search Report for PCT Patent Application No. PCT/US2007/073075, dated Nov. 13, 2008, 6 pages.

* cited by examiner

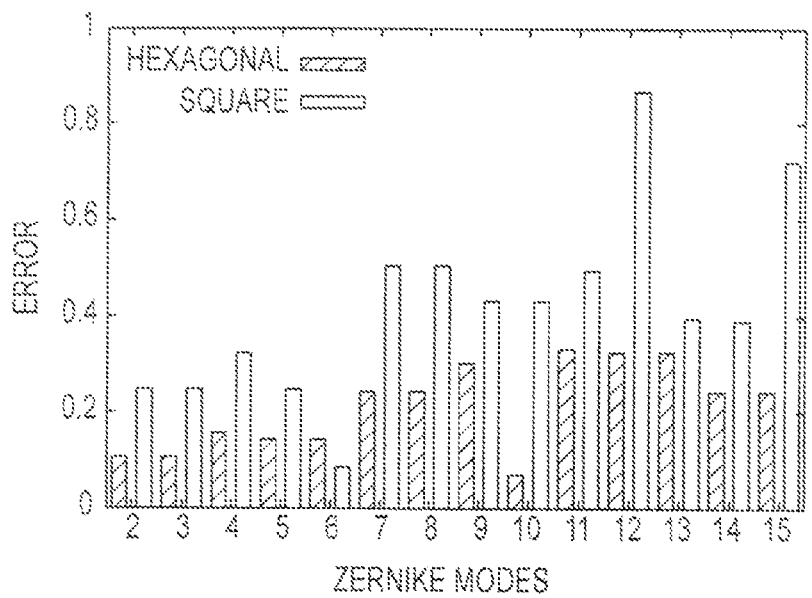
FIG.12A
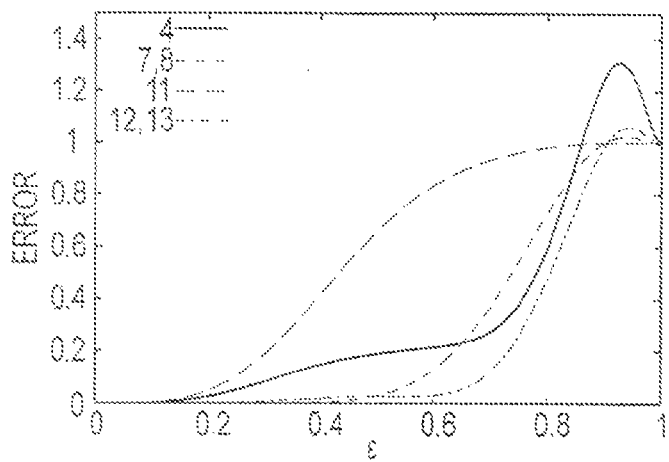
FIG.12B(i)
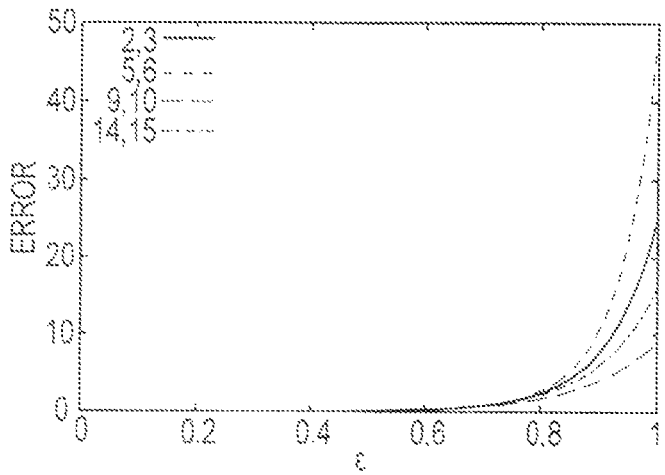
FIG.12B(ii)

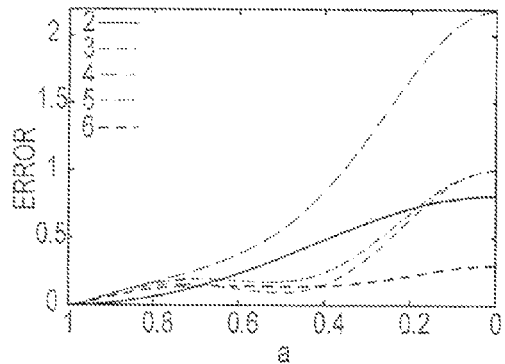
FIG.12C(i)
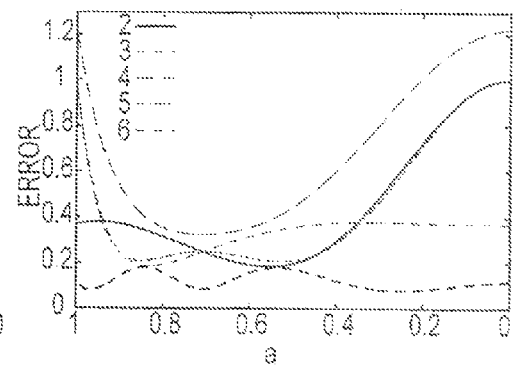
FIG.12D(i)
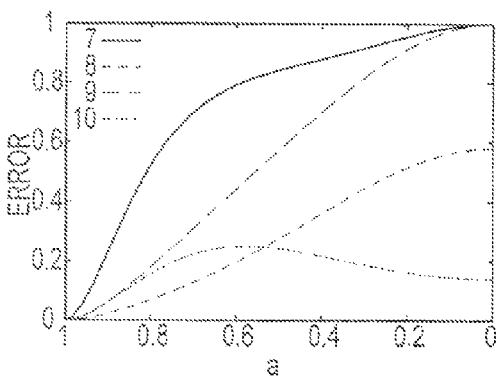
FIG.12C(ii)
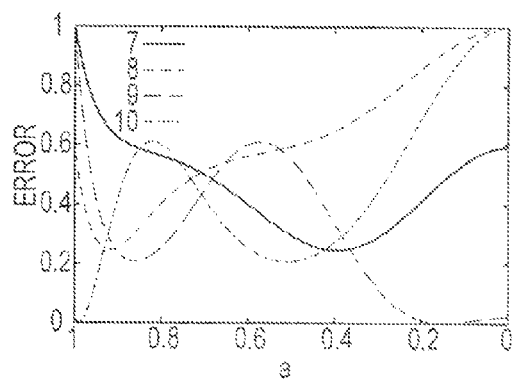
FIG.12D(ii)
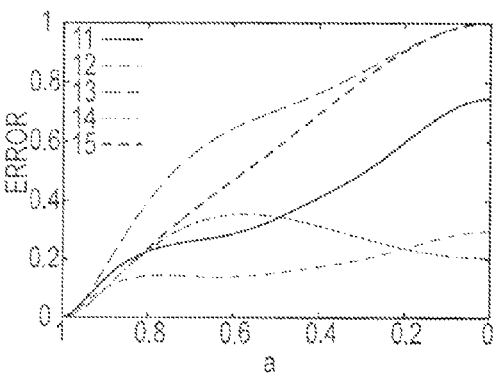
FIG.12C(iii)
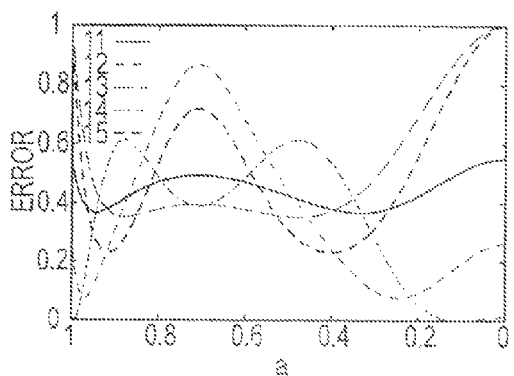
FIG.12D(iii)

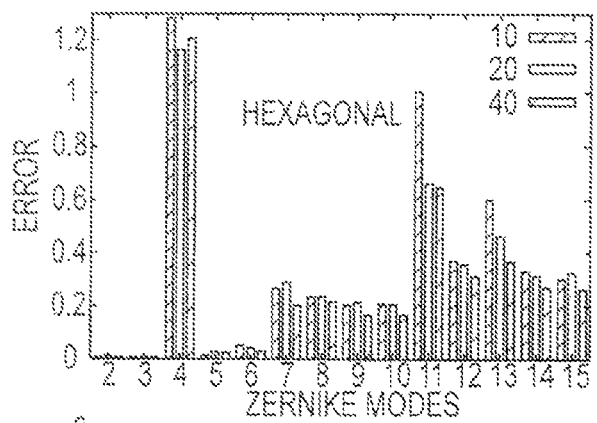
FIG.14A
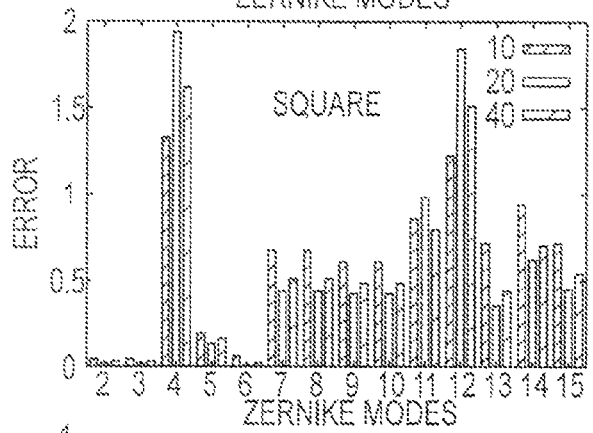
FIG.14B
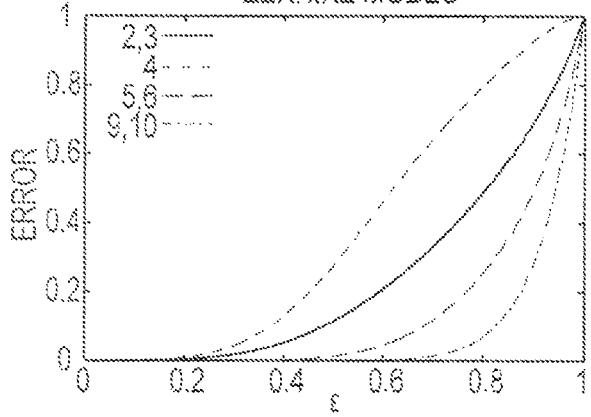
FIG.14C(i)
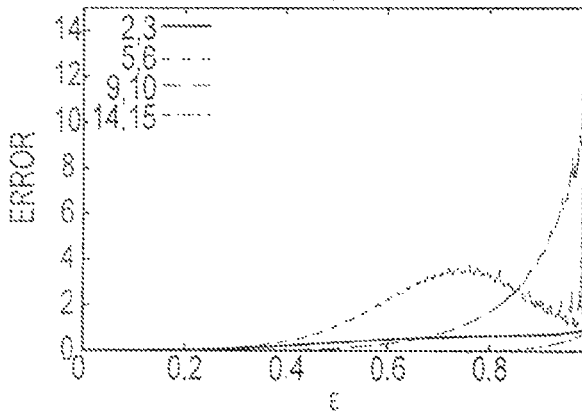
FIG.14C(ii)

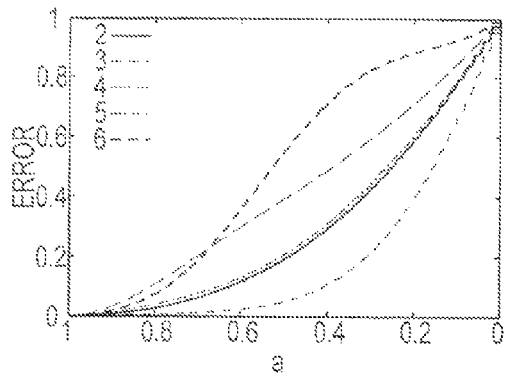
FIG.14D(i)
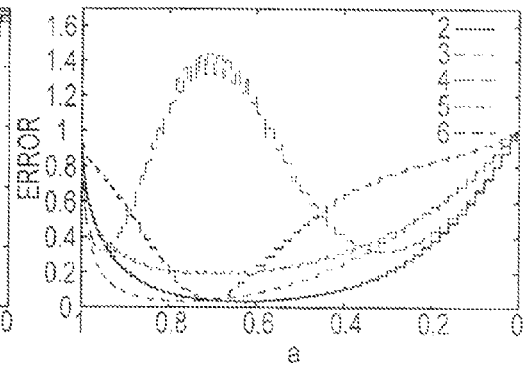
FIG.14E(i)
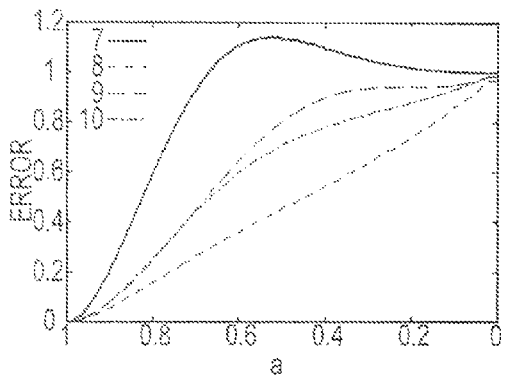
FIG.14D(ii)
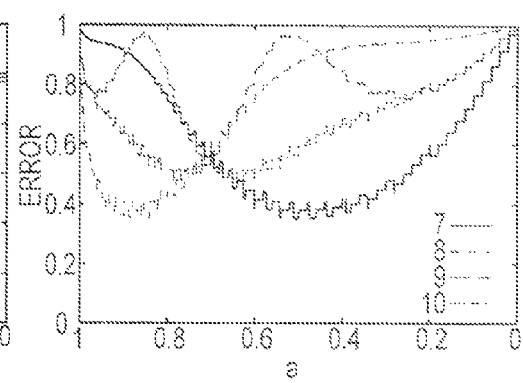
FIG.14E(ii)
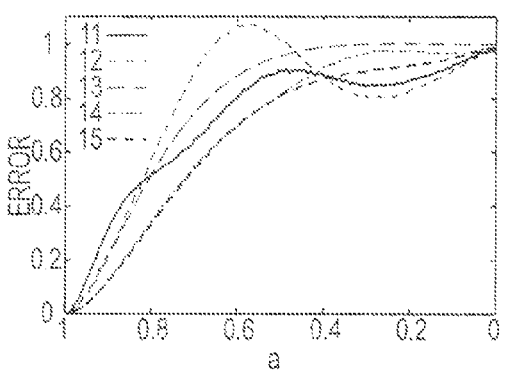
FIG.14D(iii)
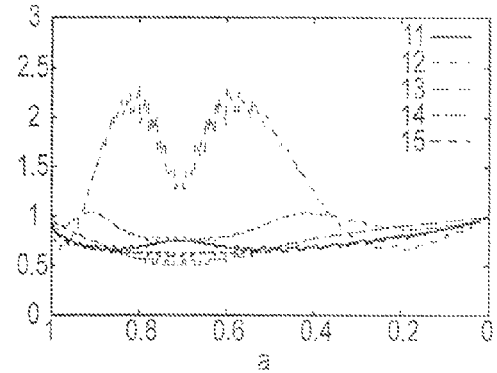
FIG.14E(iii)

US 8,983,812 B2

SYSTEMS AND METHODS FOR WAVEFRONT ANALYSIS OVER CIRCULAR AND NONCIRCULAR PUPILS

CROSS-REFERENCES TO RELATED APPLICATIONS

This application is a continuation of Ser. No. 11/775,412 filed Jul. 10, 2007, which is a nonprovisional of, and claims the benefit of the filing date of, U.S. Provisional Patent Application No. 60/819,587 filed Jul. 10, 2006, the entire disclosures of which are incorporated herein by reference for all purposes.

BACKGROUND OF THE INVENTION

Embodiments of the present invention generally relate to systems and methods for determining a set of orthonormal polynomials from a complete set of non-orthogonal polynomials over a circular or noncircular pupil. More particularly, embodiments relates to systems, methods, and software for wavefront analysis in optical design and testing for wavefront representation.

An optical system for imaging or propagation of laser beams generally has a circular pupil. It is quite common to analyze the aberrations of such a system with Zernike circle polynomials, which are orthogonal across a unit circle. However, often the pupil is circular for on-axis point objects only. For off-axis point objects, the pupil can be elliptical or irregular because of vignetting. For large optical systems, the primary mirror may be segmented, where each segment is hexagonal. Similarly, high-power laser beams may have rectangular or square cross sections. The use of circle polynomials for such cases may not be appropriate. Thus, there is a need for polynomials that are orthogonal over noncircular pupils.

Since the circle polynomials form a complete set, in principle, the aberration function can be expressed in terms of them regardless of the shape of the pupil. However, such an expansion can take a large number of terms and the advantages of orthogonality may be lost. For example, the expansion coefficients may not be independent of each other and their values may change as the number of aberration terms changes. Moreover, the variance of the aberration may not be equal to the sum of the squares of the aberration coefficients. Moreover, their physical significance may not be of much use since they may not correspond to balanced aberrations.

In practice, the aberrations of a system can be determined either by tracing rays through it or by testing it interferometrically. Thus, the aberrations may be known only at a discrete set of points, and the coefficients thus obtained may be in error even for an axial point object, since the Zernike circle polynomials, which are orthogonal over the full circular region, may not be orthogonal over the discrete points of the aberration data set.

Therefore, in light of above, it would be desirable to provide improved methods, systems, and software for determining a set of orthonormal polynomials over noncircular pupils or the discrete data set and techniques for obtaining the orthonormal aberration coefficients. Embodiments of the present invention provide solutions for at least some of these needs.

BRIEF SUMMARY OF THE INVENTION

Advantageously, embodiments of the present invention provides systems, methods, and software for determining a set of orthonormal polynomials over a noncircular pupil from a complete set of polynomials using analytical and numerical approaches. Embodiments of the present invention can be generally useful for reducing the error in wavefront fitting and reconstruction due to the incorrect use of non-orthogonal polynomials, such as Zernike circle polynomials as described by V. N. Mahajan, *Optics Imaging and Aberrations*, Part II: *Wave Diffraction Optics* (SPIE, 2004 Printing), the full disclosures of which are incorporated herein by reference. Embodiments of the present invention can provide enhanced accuracy of wavefront information in data reduction in optical design and testing.

Moreover, embodiments of the present invention can be readily adapted for use with existing wavefront analysis software in optical design and testing. One particular embodiment provides a general approach in determining of a set of orthonormal polynomials over noncircular pupils, such as an annulus, a hexagon, an ellipse, a rectangle, a square, or an irregular shape.

In one aspect, embodiments of the present invention encompass methods of determining a set of orthonormal polynomials F over a domain Σ. The method can include, for example, selecting a complete set of polynomials P as the basis for the set of orthonormal polynomials F, calculating a conversion matrix M comprising an inner product of the complete set of polynomials P over the domain Σ, and determining the set of orthonormal polynomials F based on the conversion matrix M and the complete set of polynomials P. The domain Σ may be one-dimensional, two-dimensional, or multi-dimensional. The domain Σ can be circular or noncircular. In some cases, the domain includes a noncircular pupil. Relatedly, a noncircular pupil can include an annulus, a hexagon, an ellipse, a rectangle, a square, an irregular shape, and the like. A complete set of polynomials P can include a power series. A complete set of polynomials P can include Zernike circle polynomials. A complete set of polynomials P can include a Fourier series. A complete set of polynomials P can include Taylor monomials. A complete set of polynomials P can include Jacobi polynomials. A complete set of polynomials P can include Chebyshev polynomials. A complete set of polynomials P can include Legendre polynomials. A complete set of polynomials P can include Laguerre polynomials. A complete set of polynomials P can include Hermite monomials. In some cases, an inner product of polynomials is calculated numerically as summation. In some cases, a conversion matrix M is determined by a classical Gram-Schmidt orthogonalization process. In some cases, a conversion matrix M is determined by a non-recursive method, which may involve an analytical method or a numerical method, and may involve the use of a Cholesky decomposition or a QR factorization. In some cases, a conversion matrix M is determined by a matrix transformation.

In another aspect, embodiments of the present invention encompass methods of determining a set of orthonormal polynomials over a noncircular pupil. Methods can include, for example, selecting a complete set of polynomials P as the basis for the new orthonormal polynomials F, determining a set of sub-areas of the noncircular pupil, formulating a simple relationship between x and y within each of the said sub-area such that polynomial P is integratable within each sub-area, calculating the conversion matrix M whose elements are the inner products of the complete polynomials over the noncircular pupil, and obtaining the set of orthonormal polynomials from the conversion matrix M and the complete set of basis P. A noncircular pupil can include an annulus, a hexagon, an ellipse, a rectangle, a square, an irregular shape, or the like. A complete set of polynomials P can include a power series, Zernike circle polynomials, a Fourier series, Taylor monomials, Jacobi polynomials, Chebyshev polynomials, Legendre polynomials, Laguerre polynomials, Hermite monomials, or the like. An inner product of polynomials can be calculated numerically as summation. A conversion matrix M can be determined by a classical Gram-Schmidt orthogonalization process, a modified Gram-Schmidt orthogonalization process, a non-recursive method, or a matrix transformation. A non-recursive method can include an analytical method or a numerical method. A non-recursive method can involve the use of a Cholesky decomposition or a QR factorization.

In another aspect, embodiments of the present invention provide a computer program stored on a computer-readable storage medium. The computer program can include code for calculating a pre-chosen complete set of polynomials P in a discrete, pre-chosen coordinate system, code for calculating the conversion matrix M whose elements are the inner products of the complete polynomials over a domain $\Sigma$, and code for determining the set of orthonormal polynomials from the conversion matrix M and the complete set of basis P. The computer program can also include code for integrating over the noncircular pupil of the inner products of the complete set of polynomials P symbolically. The computer program can also include code for integrating over the noncircular pupil of the inner products of the complete set of polynomials P numerically. The domain $\Sigma$ can be one-dimensional, two-dimensional, or multi-dimensional. A two-dimensional domain can be circular or noncircular. A noncircular pupil can include an annulus, a hexagon, an ellipse, a rectangle, a square, an irregular shape, or the like. A complete set of polynomials P can include a power series, Zernike circle polynomials, a Fourier series, Taylor monomials, Jacobi polynomials, Chebyshev polynomials, Legendre polynomials, Laguerre polynomials, Hermite monomials, or the like. An inner product of polynomials can be calculated numerically as summation. A conversion matrix M can be determined by a classical Gram-Schmidt orthogonalization process, a modified Gram-Schmidt orthogonalization process, a non-recursive method, or a matrix transformation. A non-recursive method can include an analytical method or a numerical method. A non-recursive method can involve the use of a Cholesky decomposition or a QR factorization.

In another aspect, embodiments of the present invention encompass a system for determining a set of orthonormal polynomials over a domain $\Sigma$. The system can include, for example, a module configured to select a complete set of polynomials P as the basis for the new orthonormal polynomials F, a module configured to calculate the conversion matrix M whose elements are the inner products of the complete polynomials over the domain $\Sigma$, and a module configured to determine the set of orthonormal polynomials from the conversion matrix M and the complete set of basis P. The domain $\Sigma$ can be one-dimensional, two-dimensional, or multi-dimensional. A two-dimensional domain can be circular or noncircular. A noncircular pupil can include an annulus, a hexagon, an ellipse, a rectangle, a square, an irregular shape, or the like. A complete set of polynomials P can include a power series, Zernike circle polynomials, a Fourier series, Taylor monomials, Jacobi polynomials, Chebyshev polynomials, Legendre polynomials, Laguerre polynomials, Hermite monomials, or the like. An inner product of polynomials can be calculated numerically as summation. A conversion matrix M can be determined by a classical Gram-Schmidt orthogonalization process, a modified Gram-Schmidt orthogonalization process, a non-recursive method, or a matrix transformation. A non-recursive method can include an analytical method or a numerical method. A non-recursive method can involve the use of a Cholesky decomposition or a QR factorization.

In another aspect, embodiments of the present invention encompass a system for determining a set of orthonormal polynomials over a noncircular pupil. The system can include, for example, a module configured to select a complete set of polynomials P as the basis for the new orthonormal polynomials F, a module configured to determine a set of sub-areas of the noncircular pupil, a module configured to formulate a simple relationship between x and y within each of the sub-area such that polynomial P is integratable within each sub-area, a module configured to calculate a conversion matrix M whose elements are the inner products of the complete polynomials over the noncircular pupil, and a module configured to determine the set of orthonormal polynomials from the conversion matrix M and the complete set of basis P.

For a fuller understanding of the nature and advantages of the present invention, reference should be had to the ensuing detailed description taken in conjunction with the accompanying drawings.

BRIEF DESCRIPTION OF THE DRAWINGS

FIG. 12A illustrates wavefront fitting error as a function of terms for hexagonal and square domains according to embodiments of the present invention.

FIGS. 12B(i) and 12B(ii) illustrate wavefront fitting error as a function of obscuration ratio for various terms for an annular domain according to embodiments of the present invention.

FIGS. 12C(i), 12C(ii), and 12C(iii) illustrate wavefront fitting error as a function of aspect ratio for various terms for an elliptical domain according to embodiments of the present invention.

FIGS. 12D(i), 12 D(ii), and 12 D(iii) illustrate illustrates wavefront fitting error as a function of aspect ratio for various terms for a rectangular domain according to embodiments of the present invention.

FIG. 14A illustrates wavefront reconstruction error as a function of terms for a hexagonal domain according to embodiments of the present invention.

FIG. 14B illustrates wavefront reconstruction error as a function of terms for a square domain according to embodiments of the present invention.

FIGS. 14C(i) and 14C(ii) illustrate wavefront reconstruction error as a function of obscuration ratio for various terms for an annular domain.

FIGS. 14D(i), 14D(ii), and 14D(iii) illustrate wavefront reconstruction error as a function of aspect ratio for various terms for an elliptical domain according to embodiments of the present invention.

FIGS. 14E(i), 14E(ii), and 14E(iii) illustrate wavefront reconstruction error as a function of aspect ratio for various terms for a rectangular domain according to embodiments of the present invention.

DETAILED DESCRIPTION OF THE INVENTION

Figure 1:
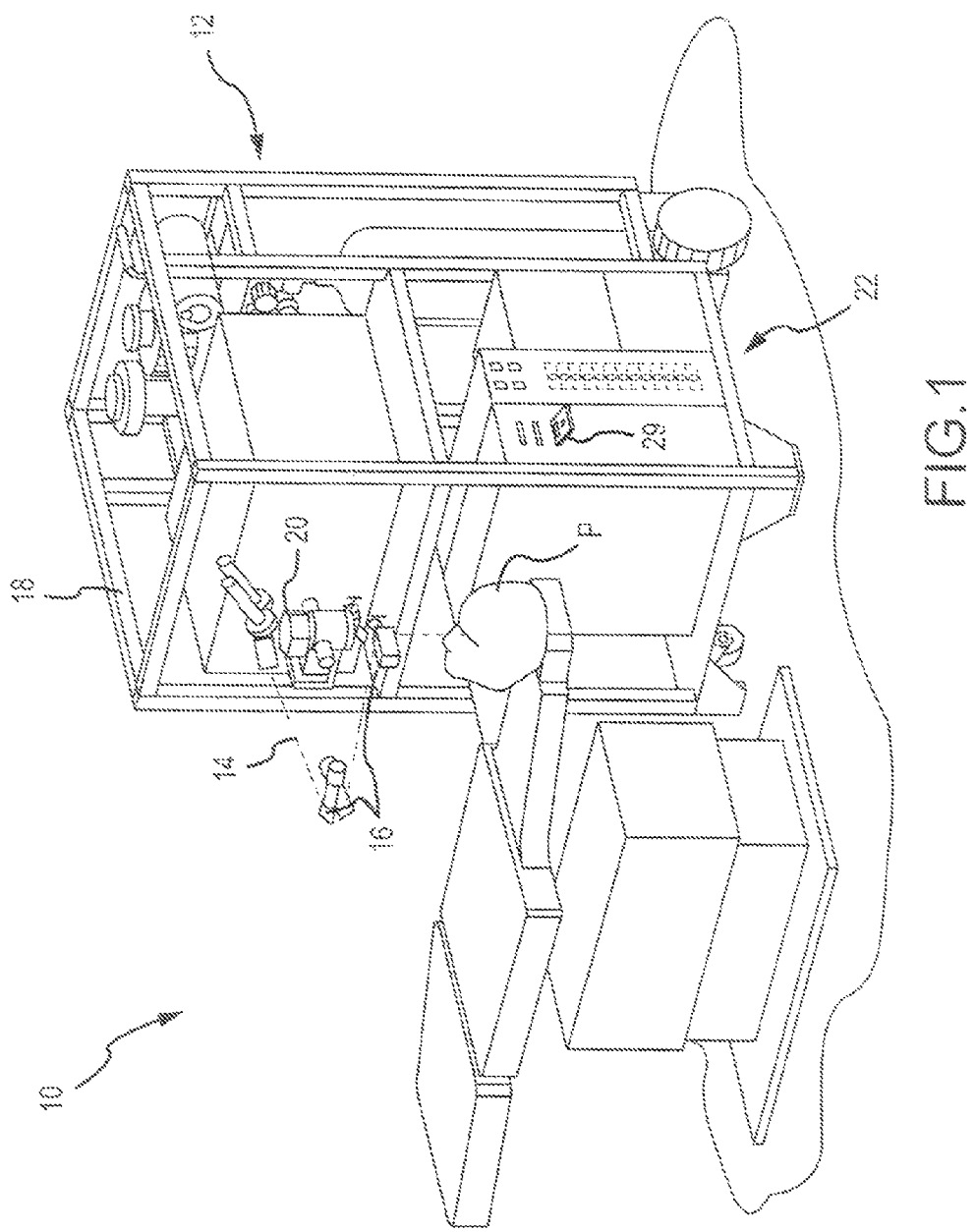
FIG. 1 illustrates a laser ablation system according to an embodiment of the present invention.

Embodiments of the present invention can be readily adapted for use with existing laser systems, wavefront measurement systems, and other optical measurement devices. Although the systems, software, and methods of the present invention are described primarily in the context of a laser eye surgery system, it should be understood the present invention may be adapted for use in alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy.

Embodiments of the present invention involve the representation of ocular aberrations. In some cases, embodiments involve the representation of aberrations in other optical systems. Often, Zernike polynomials, circle polynomials, or Zernike circle polynomials are used to characterize ocular aberrations. Such polynomials are orthogonal over a circular pupil. Embodiments of the present invention provide polynomials that are orthogonal over any of a variety of shapes. These polynomials can be used with optical systems that have a pupil or aperture that is circular or noncircular. For example, these polynomials can be used with human eyes that have elliptical or irregularly shaped pupils. Similarly, these polynomials can be used with optical systems such as telescopes which may have hexagonal apertures. Relatedly, these polynomials can be used with optical systems such as high power lasers which may have square or rectangular apertures. It is understood that these polynomials can be used with any of a variety of optical devices. Embodiments of the present invention provide sets of polynomials, where each is orthonormal over a specific pupil or aperture. For example, some embodiments provide a set of elliptical polynomials for use with an elliptical pupil or aperture. Some embodiments provide a set of rectangular polynomials for use with a rectangular pupil or aperture. Polynomials may be orthonormal, which can be defined as orthogonal and normal. Orthonormal polynomials can have various properties. For example, the truncation of the wavefront expansion may not change the expansion coefficients. In some embodiments, each orthonormal polynomial except for the piston term has a mean value of zero. Further, a wavefront mean value can equal the piston coefficient. In some embodiments, each orthonormal polynomial has a minimum variance. What is more, a wavefront variance can be the sum of squares of each expansion coefficient, excluding the piston coefficient. Embodiments of the present invention provide methods for establishing or constructing orthonormal polynomials over pupils or apertures having various shape. These sets of polynomials can be orthonormal over their respective pupil or aperture shape. In some embodiments, the terms "pupil" and "aperture" can be used interchangeably.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
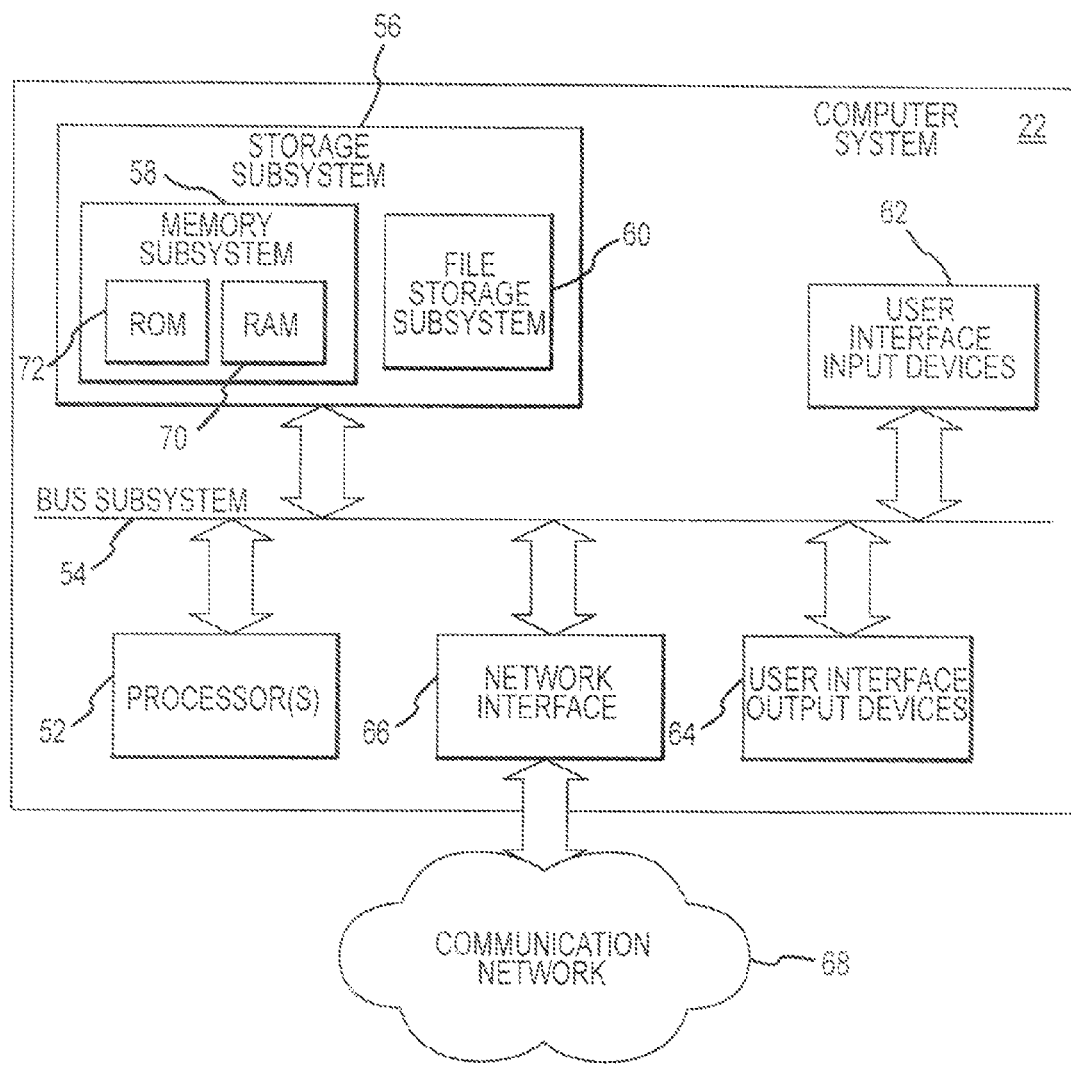
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
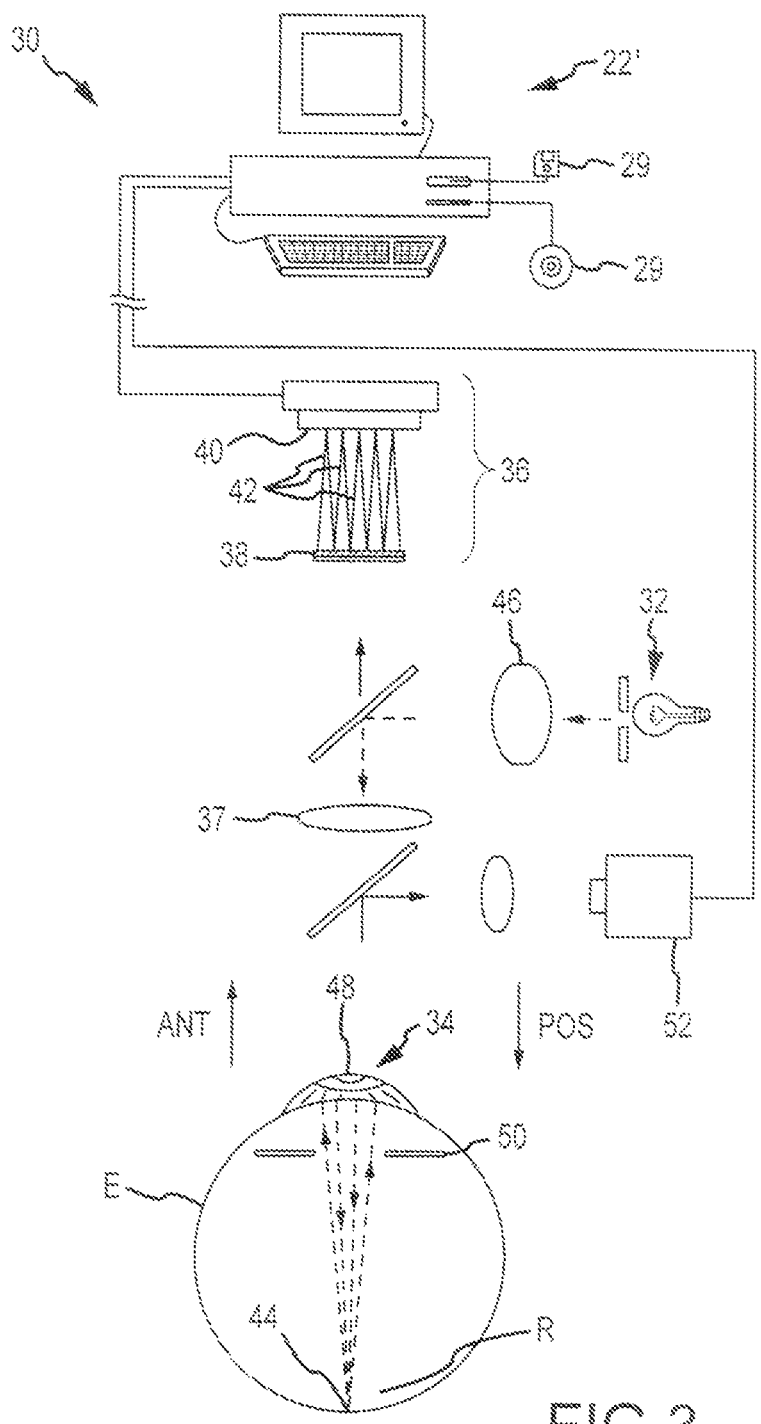
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
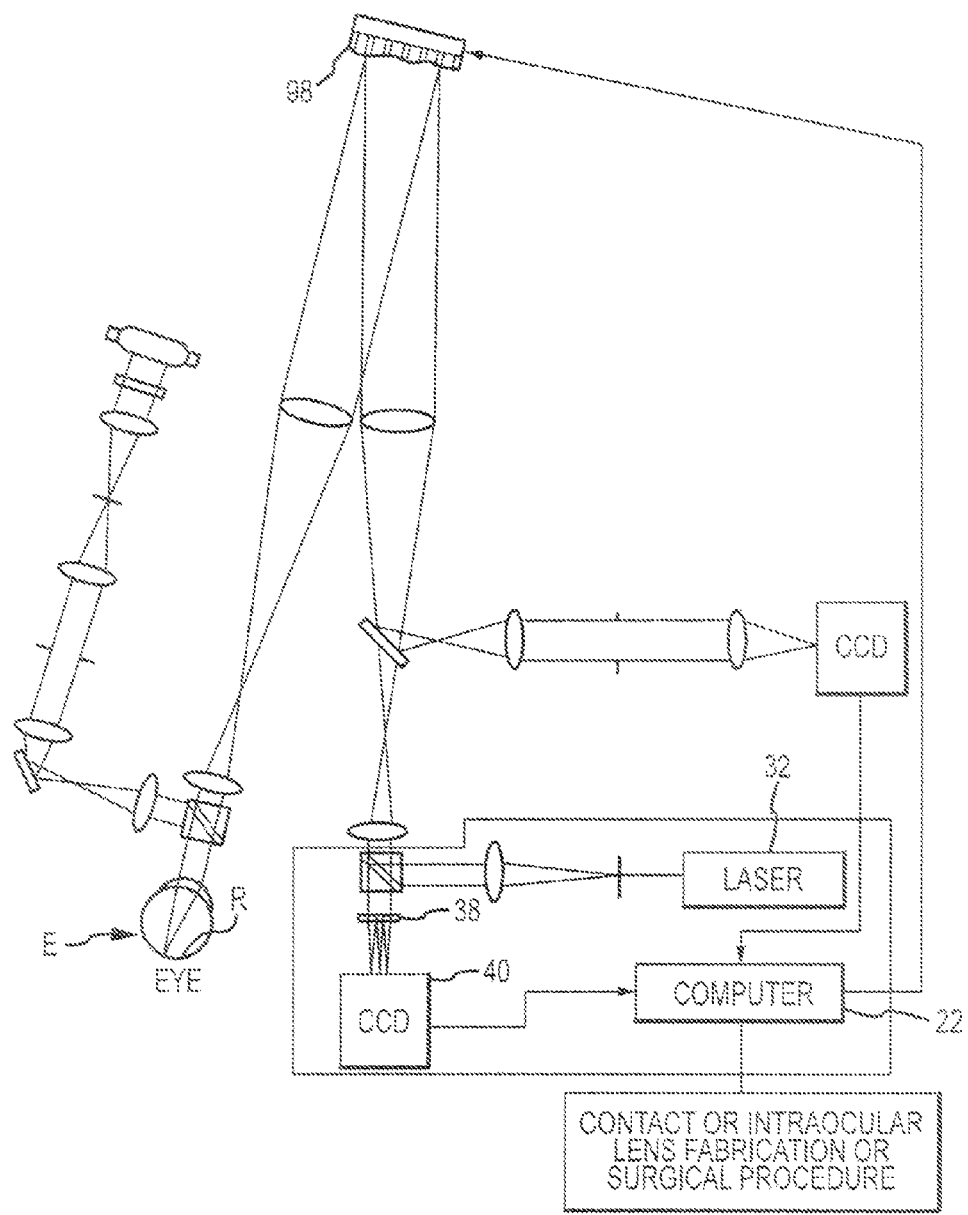
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from VISX, INCORPORATED of Santa Clara, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like.

Figure 4:
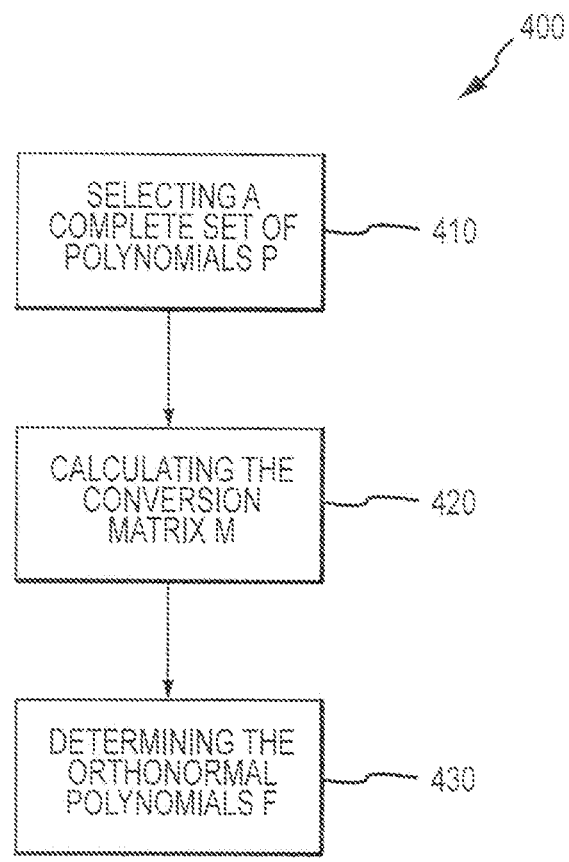
FIG. 4 is a flow chart that schematically illustrates a method of determining a set of orthonormal polynomials according to embodiments of the present invention.

Referring now to FIG. 4, embodiments of the present invention encompass a method 400 of determining orthonormal polynomials. For example, the method can include selecting a set of complete polynomials (P) as indicated by step 410, where the set of complete polynomials (P) can be a set of Zernike circle polynomials, power series, Fourier series, or Taylor monomials. The method can also include calculating a real, lower triangle matrix (M) as indicated by step 420, where the matrix relates the complete set of polynomials (P) to the set of orthonormal polynomials (F). The method can also include determining the set of orthonormal polynomials (F) as indicated by step 430, by using the conversion matrix (M) and the complete set of non-orthonormal polynomials (P). In another particular embodiment, the present invention provides a general approach in determination of a set of orthonormal polynomials over the noncircular pupils using an analytical or a numerical approach.

Figure 5:
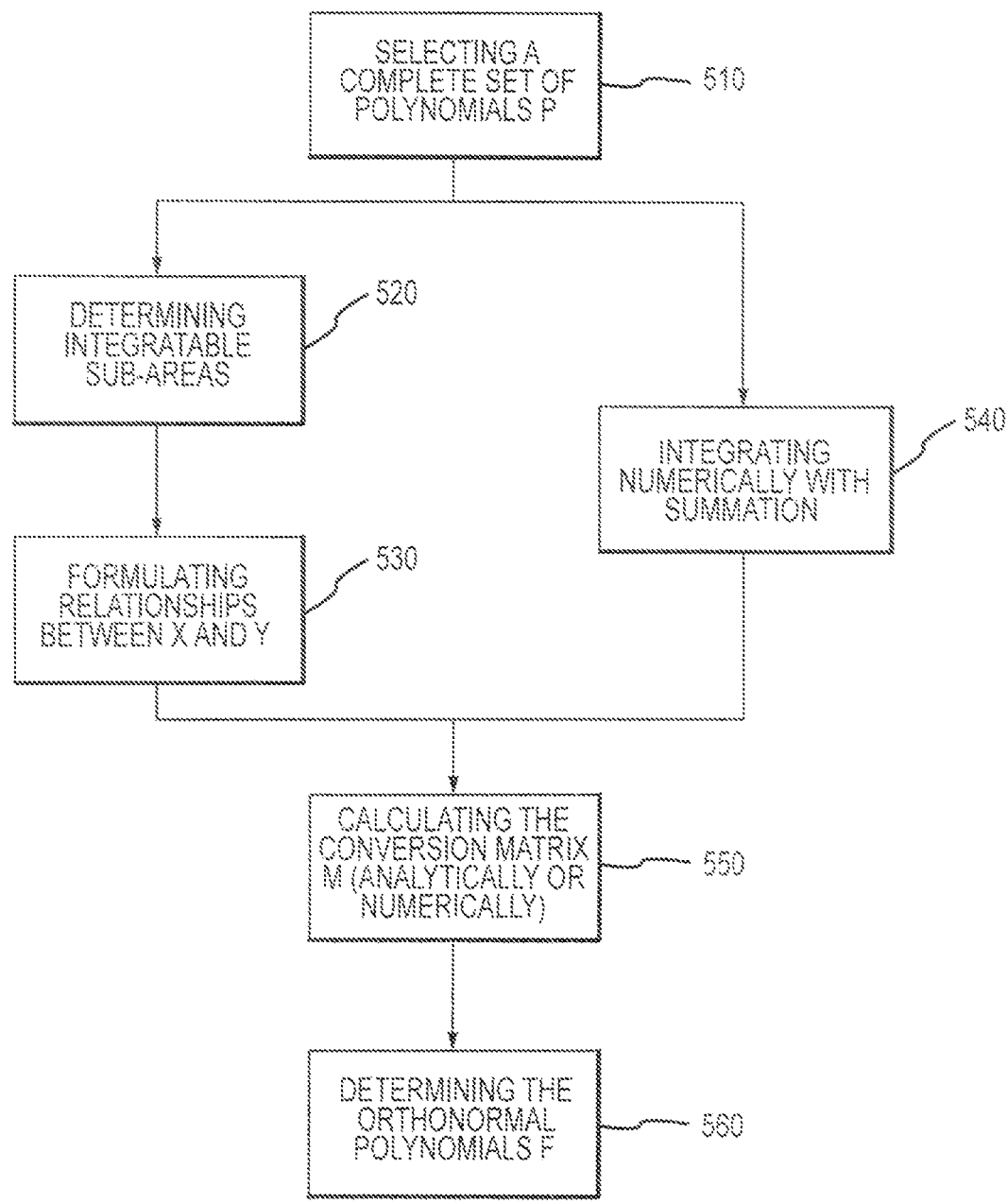
FIG. 5 is a flow chart that schematically illustrates a method of determining a set of orthonormal polynomials using analytical and numerical processes according to embodiments of the present invention.

Referring to FIG. 5, embodiments of the present invention encompass a method 500 of determining orthonormal polynomials. For example, the method can include selecting a set of complete polynomials (P) for a particular domain as indicated by step 510. The set of complete polynomials (P) can be a set of Zernike circle polynomials, power series, Fourier series, or Taylor monomials. The method can also include selecting a set of sub-areas within the domain as indicated by step 520 so that the complete set of polynomials (P) is integratable over the domain. Further, the method can include formulating or constructing a simple relationship between x and y, as indicated by step 530, so the two-dimensional integration can be reduced to one-dimensional integration. In this way, the elements in conversion matrix (M) can be calculated analytically as indicated by step 550. Alternatively, if the domain is not integratable in closed form, the integration can be performed numerically using summation of the discrete data, as indicated by step 540. Similarly the conversion matrix (M) can be calculated numerically as indicated by step 540. As indicated by step 560, the method can include determining or obtaining the set of orthonormal polynomials (F) by using the conversion matrix (M) and the complete set of polynomials (P).

A. Complete Set of Polynomials

A complete set of polynomials can be defined as a set of polynomials with which any function or polynomial term can be accurately represented without error. A complete set of polynomials can be the set of Zernike circle polynomials, power series, Fourier series, and Taylor monomials. It can also be any other polynomials such as Jacobi polynomials, Chebyshev polynomials, Legendre polynomials, Laguerre polynomials, Hermite polynomials, and the like. A complete set of polynomials can be a series that can continue indefinitely.

Zernike circle polynomials can be a complete set of polynomials that is orthogonal over circular pupils. Their use in optical design and testing is appropriate and effective when the pupil is circular. However, when the pupil is noncircular, their use may not be appropriate. Zernike circle polynomials can be defined as $$Z_j(\rho,\theta)=Z_n^m(\rho,\theta)=R_n^m(\rho)\Theta^m(\theta), \quad (1)$$

where j is the single-index and n and m are the double-index. n can be referred to as the radial degree and m as the azimuthal frequency. Typically, n−m is even and n−m≥0. The Zernike radial polynomials are related to Jacobi polynomials and can be expressed analytically as $$R_n^m(\rho) = \sum_{s=0}^{(n-m)/2} \frac{(-1)^s \sqrt{(n+1)(2-\delta_{m0})}\,(n-s)!}{s!\,[(n+m)/2-s]!\,[(n-m)/2-s]!} \rho^{n-2s} \quad (2)$$

and the triangular function is $$\Theta^m(\theta) = \begin{cases} \cos m\theta & \text{(even/term)} \\ \sin m\theta & \text{(odd/term)} \\ 1 & (m=0) \end{cases} \quad (3)$$

However, we can also use power series $$P_j(\rho,\theta) = P_n^m(\rho,\theta) = \rho^n \Theta^m(\theta) \quad (4)$$

to represent any function, because the set of power series is also a complete set. There may be advantages to using power series. First, it is a set of monomials, so it is simple. Second, any function can be naturally expressed as a function of $\rho$ and $\theta$, when it is expressed as a linear combination of power series. Other immediate complete sets of polynomials include Fourier series and Taylor monomials. Fourier series are often defined as sinusoidal functions that can be easily implemented with fast Fourier transforms. Taylor monomials are similar to power series. They can be expressed as $$F_u^v(x,y) = \exp\left[j\frac{2\pi}{N}(ux+vy)\right], \quad (5)$$

$$T_p^q(x,y) = x^q y^{p-q} \quad (6)$$

where u and v are the variables in the frequency domain, and p and q are the radial degree and azimuthal frequency, respectively.

In some embodiments, any continuous function, such as a wavefront, can be expressed in terms of any complete set of polynomials. For example, a wavefront can be expressed in terms of Zernike circle polynomials or power series as $$W(\rho,\theta) = \sum_{j=1}^{\infty} a_j Z_j(\rho,\theta), \quad (7)$$

$$W(\rho,\theta) = \sum_{j=1}^{\infty} b_j P_j(\rho,\theta). \quad (8)$$

where $a_j$ and $b_j$ are the expansion coefficients, respectively.

B. Determination of Orthonormal Polynomials

As discussed above, when the pupil is noncircular, Zernike polynomials may not be an appropriate set of polynomials for wavefront analysis. For aberration balancing to obtain minimum variance, it may be helpful to construct a set of orthonormal polynomials over a certain noncircular pupil.

Many noncircular pupils are common in practice. Annular, hexagonal, elliptical, rectangular, and square pupils are common. Irregular pupil shapes can also be common due to vignetting of rays. Examples of irregular pupil shapes are shown in FIGS. 6A to 6F. Suppose we define a noncircular domain as $\Sigma$. Embodiments of the present invention encompass methods of constructing a set of polynomials F that are orthonormal over the domain $\Sigma$.

The inner product of two terms from two polynomials $F_j$ and $G_{j'}$ can be defined as $$\langle F_j | G_{j'} \rangle = \frac{1}{A}\int_\Sigma F_j G_{j'} d^2 s, \quad (9)$$

where A is the area of the domain $\Sigma$. The orthonormality of F can be expressed as $$\langle F_j | F_{j'} \rangle = \delta_{jj'}, \quad (10)$$

where $\delta_{jj'}$ is the Kronecker symbol.

Recursive and non-recursive approaches can be used to determine F. A recursive approach is the Gram-Schmidt orthogonalization process, and a non-recursive approach is a matrix transformation approach.

1. The Gram-Schmidt Orthogonalization Process

Because any continuous function can be expressed as linear combination of a complete set of polynomials, we may write $$F_l(x,y) = \sum_{j=1}^{l} M_{ij} P_j(x,y), \quad (11)$$

where M is a conversion matrix relating the orthonormal polynomials F to P. Calculation of F can be done either recursively by:

$$F_1 = G_1 = P_1, \quad (12a)$$

$$G_{i+1} = \sum_{k=1}^{i} c_{i+1,k} F_k + P_{i+1}, \quad (12b)$$

$$F_{i+1} = G_{i+1}[\langle G_{i+1} | G_{i+1} \rangle]^{-1/2}, \quad (12c)$$

where $$c_{i+1,k} = -\langle P_{i+1} | F_k \rangle. \quad (12d)$$

We now show how to derive a set of orthonormal polynomials over circular pupils from the set of power series, according to some embodiments of the present invention. Because the domain is a unit circle, the integration will be for the unit circle. The area A is $\pi$. Following the process in Eqs. (12), we have $$F_1 = G_1 = P_1 = 1. \quad (13a)$$

$$c_{2,1} = -\langle P_2|F_1\rangle = -\langle \rho\cos\theta\rangle = 0, \quad (13b)$$

$$G_2 = P_2 = \rho\cos\theta, \quad (13c)$$

$$F_2 = G_2[\langle (G_2|G_2)\rangle]^{-1/2} = 2G_2 = 2\rho\cos\theta. \quad (13d)$$

Continuing this process for higher terms, we obtain the next few terms as $$F_3 = 2G_3 = 2\rho\sin\theta, \quad (14a)$$

$$F_4 = 2\sqrt{3}\left(P_4 + \frac{1}{2}P_1\right) = \sqrt{3}(2\rho^2 - 1), \quad (14b)$$

$$F_5 = \sqrt{6}\,G_5 = \sqrt{6}\,\rho^2\sin 2\theta, \quad (14c)$$

$$F_6 = \sqrt{6}\,G_6 = \sqrt{6}\,\rho^2\cos 2\theta. \quad (14d)$$

It is quite clear that this set of orthonormal polynomials F can be exactly the same as the orthonormal Zernike circle polynomials. Thus, they can be derived from the power series using the Gram-Schmidt orthogonalization process.

Figure 6A:
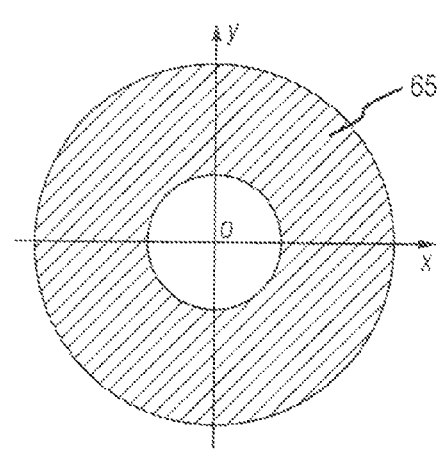
FIG. 6A schematically illustrates an annular domain and its sub-areas according to embodiments of the present invention.
Figure 7:
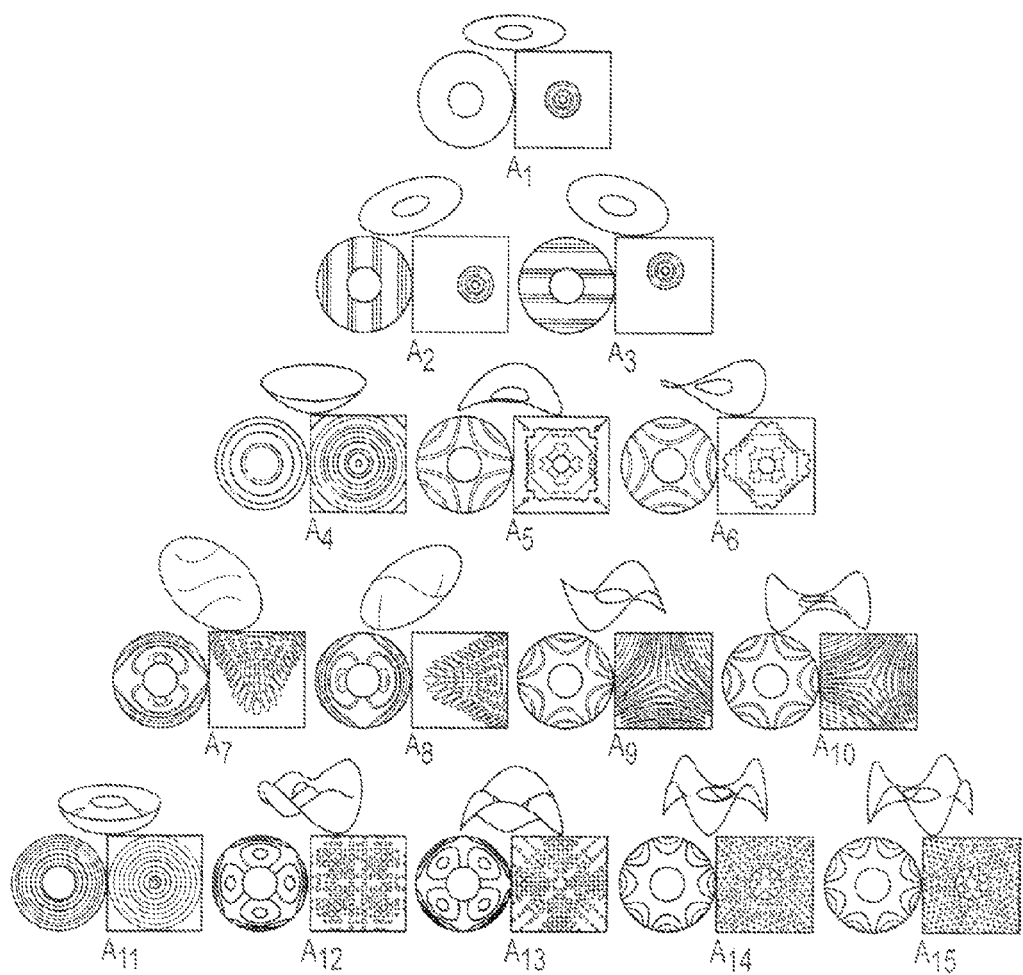
FIG. 7 illustrates the isometric plots, interferograms, and point spread functions of annular polynomials of the first 4 orders, where an obscuration ratio $\epsilon=0.35$, according to embodiments of the present invention.

For noncircular pupils, the procedure is the same, according to some embodiments. A first example is an annular pupil, as shown in FIG. 6A. The integration limits for sub-area 650A are simply [1,ϵ; 0,2π] in polar coordinates. The area A is $\pi(1-\epsilon^2)$. Zernike annular polynomials have been constructed by means of the Gram-Schmidt orthogonalization process by V. N. Mahajan, "Zernike annular polynomials for imaging systems with annular pupils," J. Opt. Soc. Am. 71, 75-86 (1981), the full disclosure of which is incorporated herein by reference. FIG. 7 shows the isometric plots (top), interferograms (left), and point-spread functions (right) of the first 4 orders of Zernike annular polynomials $A_1$ through $A_{15}$.

Figure 6B:
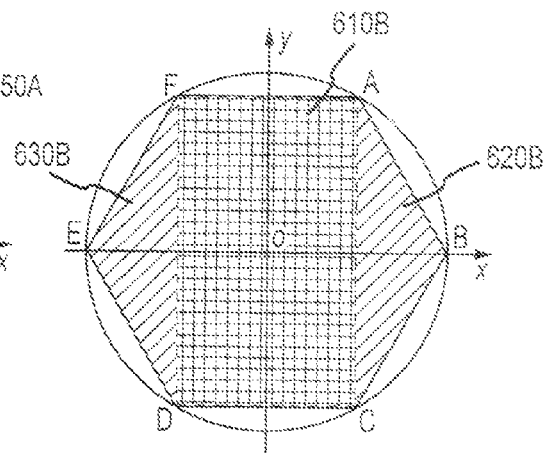
FIG. 6B schematically illustrates a hexagonal domain and its sub-areas according to embodiments of the present invention.

As another example, for hexagonal pupils, as shown in FIG. 6B, the inner product can involve integration over the unit hexagon. To do the integration, we divide the hexagon into three sub-areas, rectangular ACDF 610B, and two similar triangles ABC 620B, and DEF 630B. The x and y integration limits for 610B are [−½, ½; −√3/2, √3/2]. Similarly, those for 620B and 630B are [½, 1; −√3(1−x), −√3(1−x)] and [−1,−½; −√3(1+x), −√3(1+x)], respectively. With these limits available, inner products of polynomials P and the hexagonal polynomials H can be calculated easily as follows:

$$H_1 = G_1 = P_1 = 1. \tag{15a}$$

$$c_{2,1} = -\langle P_2 \mid H_1 \rangle = -\langle \rho\cos\theta \rangle = 0, \tag{15b}$$

$$G_2 = P_2 = \rho\cos\theta, \tag{15c}$$

$$H_2 = G_2[\langle G_2 \mid G_2 \rangle]^{-1/2} = 2\sqrt{\frac{6}{5}}\,G_2 = 2\sqrt{\frac{6}{5}}\,\rho\cos\theta. \tag{15d}$$

Continuing this process, we obtain $$H_3 = 2\sqrt{\frac{6}{5}}\,\rho\sin\theta, \tag{16a}$$

$$H_4 = \sqrt{\frac{5}{43}}\,(12\rho^2 - 5), \tag{16b}$$

$$H_5 = 2\sqrt{\frac{15}{7}}\,\rho^2\sin2\theta, \tag{16c}$$

$$H_6 = 2\sqrt{\frac{15}{7}}\,\rho^2\cos2\theta. \tag{16d}$$

Figure 8:
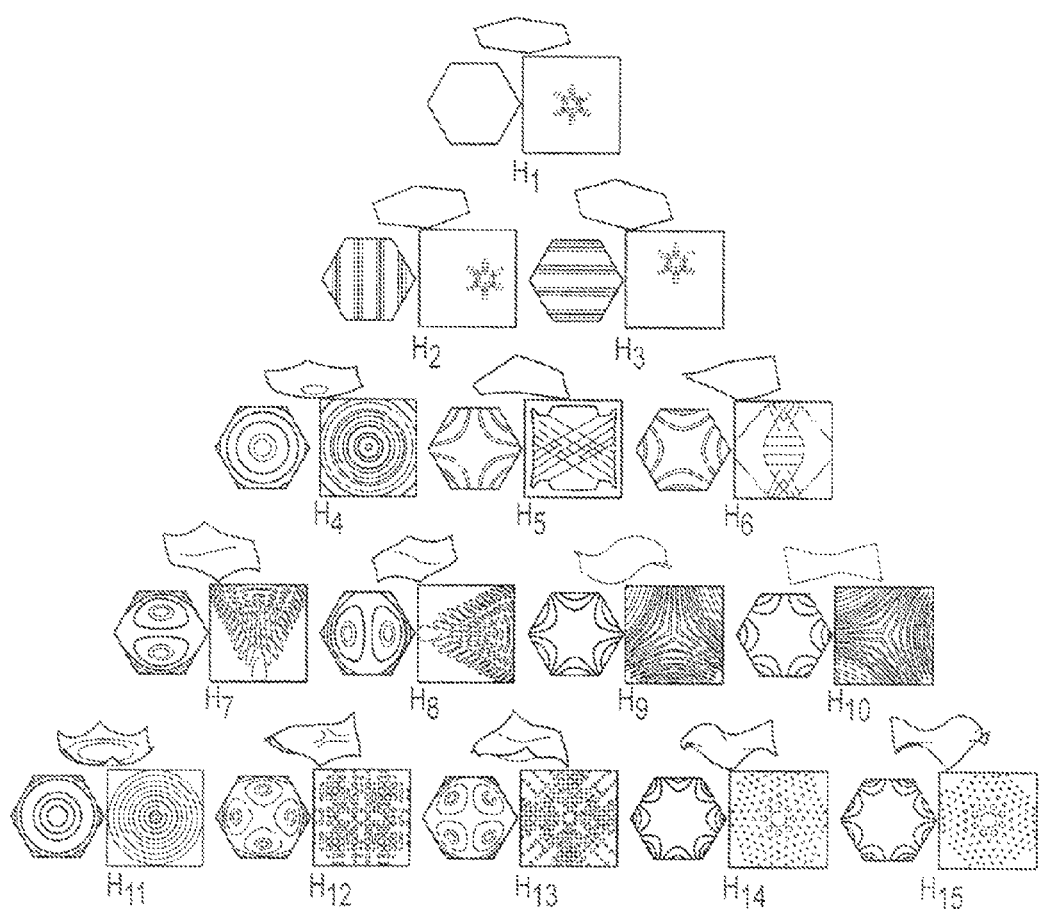
FIG. 8 illustrates the isometric plots, interferograms, and point spread functions of hexagonal polynomials of the first 4 orders according to embodiments of the present invention.

The isometric plots (top), interferograms (left), and point-spread functions (right) for the first 4 orders $H_1$ through $H_{15}$ are shown in FIG. 8.

Figure 6C:
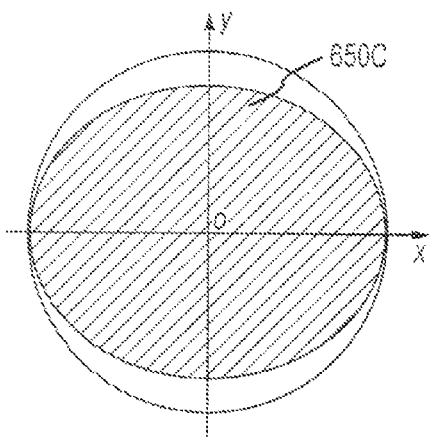
FIG. 6C schematically illustrates an elliptical domain and its sub-areas according to embodiments of the present invention.

For yet another example, for elliptical pupils, as shown in FIG. 6C, the inner product can involve integration over a unit ellipse, an ellipse that is inscribed by a unit circle.

The integration limits for sub-area 650C are $[-\sqrt{e^2-y^2}/e, \sqrt{e^2-y^2}/e; -e, e]$ in Cartesian coordinates. The area A is πe. With these limits, the inner products of polynomials P and the elliptical polynomials E can be calculated as follows:

$$E_1 = G_1 = P_1 = 1. \tag{17a}$$

$$c_{2,1} = -\langle P_2 \mid E_1 \rangle = -\langle \rho\cos\theta \rangle = 0, \tag{17b}$$

$$G_2 = P_2 = \rho\cos\theta, \tag{17c}$$

$$E_2 = G_2[\langle G_2 \mid G_2 \rangle]^{-1/2} = 2G_2 = 2\rho\cos\theta. \tag{17d}$$

Additional elliptical polynomials are given below:

$$E_2 = \frac{2}{e}\rho\sin\theta, \tag{18a}$$

$$E_4 = \sqrt{\frac{3}{3-2e^2+3e^4}}\,[4\rho^2 - (1+e^2)], \tag{18b}$$

$$E_5 = \frac{\sqrt{6}}{e}\rho^2\sin2\theta, \tag{19c}$$

$$E_6 = \frac{2\sqrt{6}}{\sqrt{3-2e^2+3e^4}}\,\rho^2\cos2\theta. \tag{19d}$$

Figure 9:
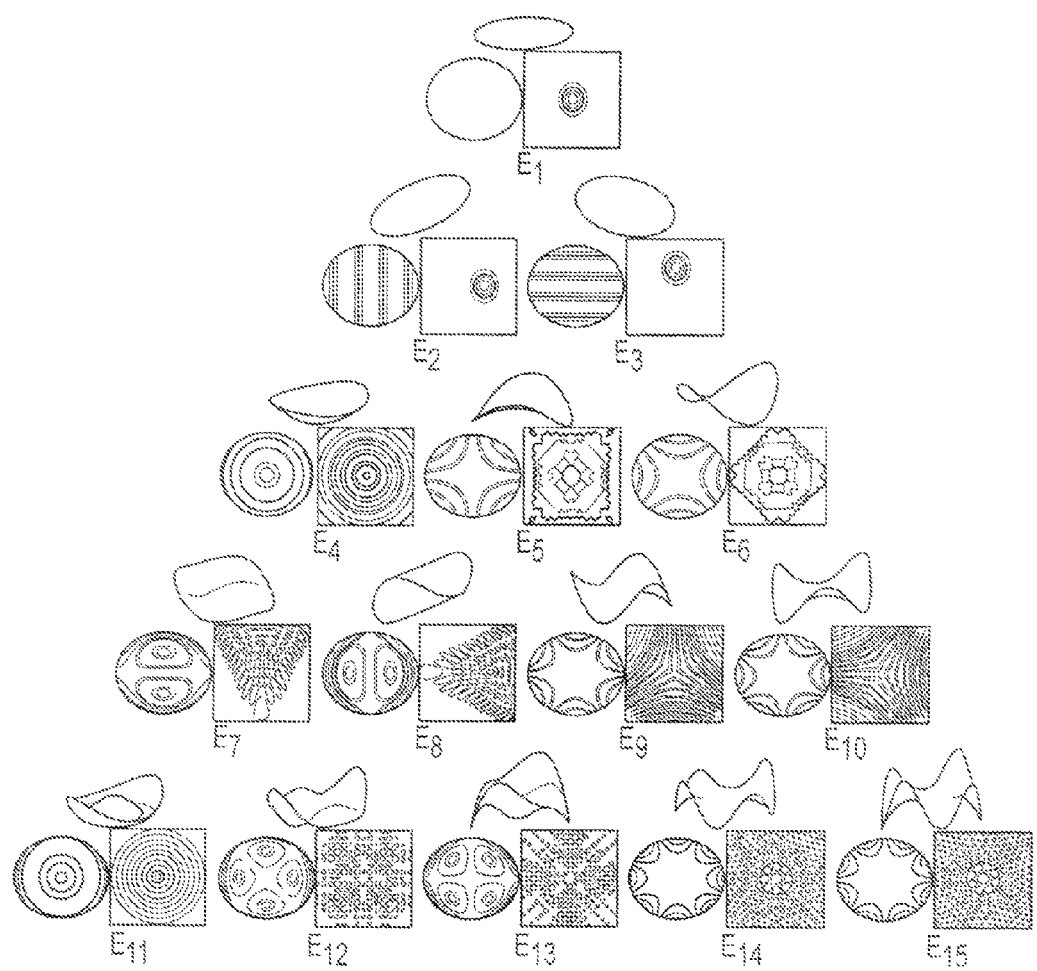
FIG. 9 illustrates the isometric plots, interferograms, and point spread functions of elliptical polynomials of the first 4 orders, where an aspect ratio $e=0.85$, according to embodiments of the present invention.

These polynomials reduce to circle polynomials as e→1. The isometric plots (top), interferograms (left), and point-spread functions (right) for the first 4 orders elliptical polynomials $E_1$ through $E_{15}$ are shown in FIG. 9.

Figure 6D:
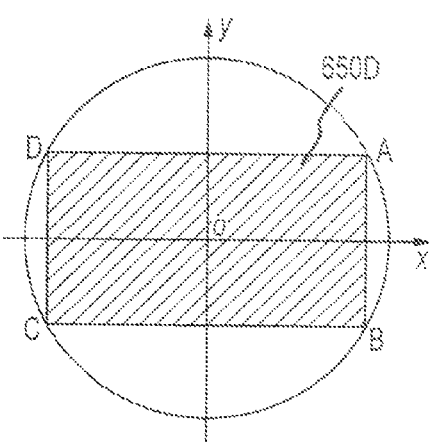
FIG. 6D schematically illustrates a rectangular domain and its sub-areas according to embodiments of the present invention.

For yet another example, for rectangular pupils, as shown in FIG. 6D, the inner product can involve integration over the unit rectangle. The integration limits for sub-area 650D are $[-a, a; -\sqrt{1-a^2}, \sqrt{1-a^2}]$ in Cartesian coordinates. The area A is $4a\sqrt{1-a^2}$. With these limits available, inner products of polynomials P and the rectangular polynomials R can be calculated easily as follows:

$$R_1 = G_1 = P_1 = 1. \tag{19a}$$

$$c_{2,1} = -\langle P_2 \mid R_1 \rangle = -\langle \rho\cos\theta \rangle = 0, \tag{19b}$$

$$G_2 = P_2 = \rho\cos\theta, \tag{19c}$$

$$R_2 = G_2[\langle G_2 \mid G_2 \rangle]^{-1/2} = \frac{\sqrt{3}}{a}G_2 = \frac{\sqrt{3}}{a}\rho\cos\theta. \tag{19d}$$

Additional rectangular polynomials are given below:

$$R_3 = \sqrt{\frac{3}{1-a^2}}\,\rho\sin\theta, \tag{20a}$$

$$R_4 = \frac{\sqrt{5}}{2\sqrt{1-2a^2+2a^4}}\,(3\rho^2 - 1), \tag{20b}$$

$$R_5 = \frac{3}{2a\sqrt{1-a^2}}\,\rho^2\sin2\theta, \tag{20c}$$

$$R_6 = \frac{3\sqrt{5}}{\sqrt{9-28a^2+28a^4}}\,\rho^2\cos2\theta. \tag{20d}$$

Figure 10:
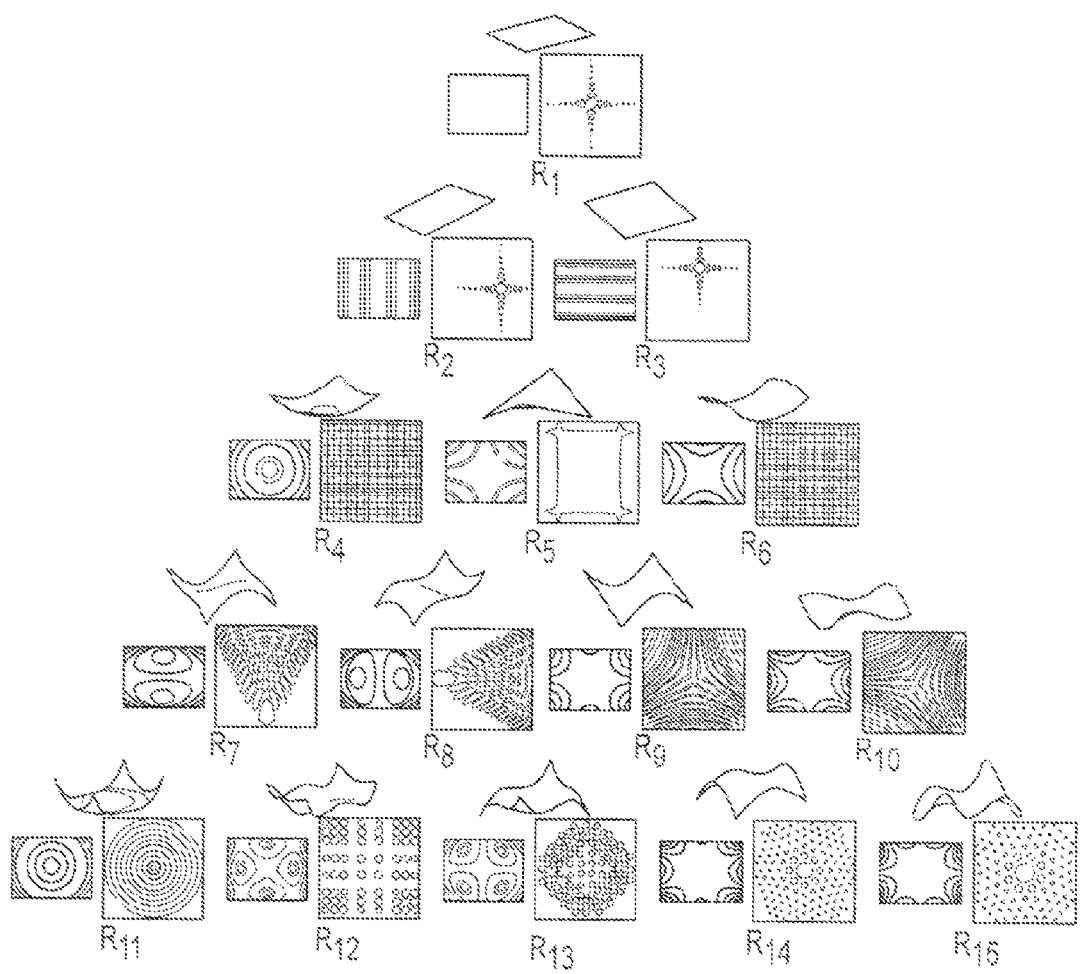
FIG. 10 illustrates the isometric plots, interferograms, and point spread functions of rectangular polynomials of the first 4 orders, where an aspect ratio a=0.8, according to embodiments of the present invention.

The isometric plots (top), interferograms (left), and point-spread functions (right) for the first 4 orders rectangular polynomials $R_1$ through $R_{15}$ are shown in FIG. 10.

Figure 6E:
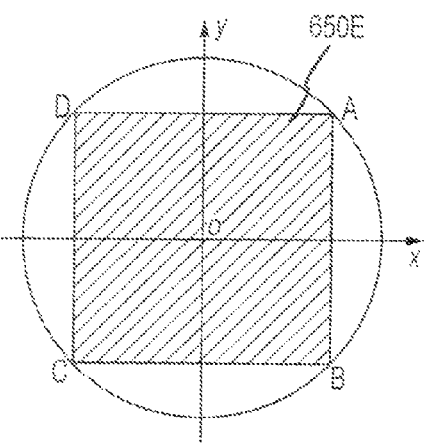
FIG. 6E schematically illustrates a square domain and its sub-areas according to embodiments of the present invention.

For yet another example, for square pupils, as shown in FIG. 6E, the inner product can involve integration over the unit square. The integration limits for sub-area 650E are $[-1/\sqrt{2}, 1/\sqrt{2}; -1/\sqrt{2}, 1/\sqrt{2}]$ in Cartesian coordinates. The area A is 2. With these limits available, inner products of polynomials P and the square polynomials S can be calculated as follows:

$$S_1 = G_1 = P_1 = 1. \tag{21a}$$

$$c_{2,1} = -\langle P_2 \mid S_1 \rangle = -\langle \rho\cos\theta \rangle = 0, \tag{21b}$$

$$G_2 = P_2 = \rho\cos\theta, \tag{21c}$$

$$S_2 = G_2[\langle G_2 \mid G_2 \rangle]^{-1/2} = \sqrt{6}\,G_2 = \sqrt{6}\,\rho\cos\theta. \tag{21d}$$

Additional square polynomials are given below:

$$S_3 = \sqrt{6}\,\rho\sin\theta, \tag{22a}$$

$$S_4 = \sqrt{\frac{5}{2}}\,(3\rho^2 - 1), \tag{22b}$$

$$S_5 = 3\rho^2\sin 2\theta, \tag{22c}$$

$$S_6 = 3\sqrt{\frac{5}{2}}\,\rho^2\cos 2\theta. \tag{22d}$$

Figure 11:
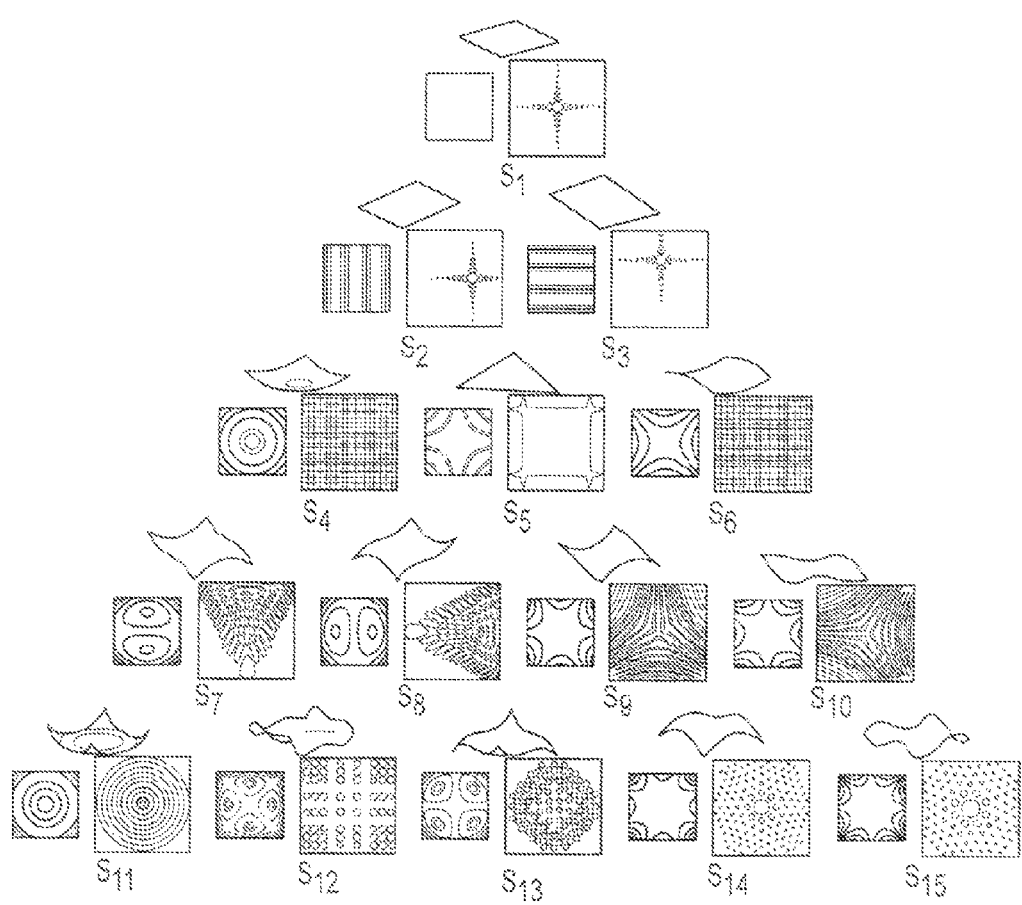
FIG. 11 illustrates the isometric plots, interferograms, and point spread functions of square polynomials of the first 4 orders according to embodiments of the present invention.
Figure 13A:
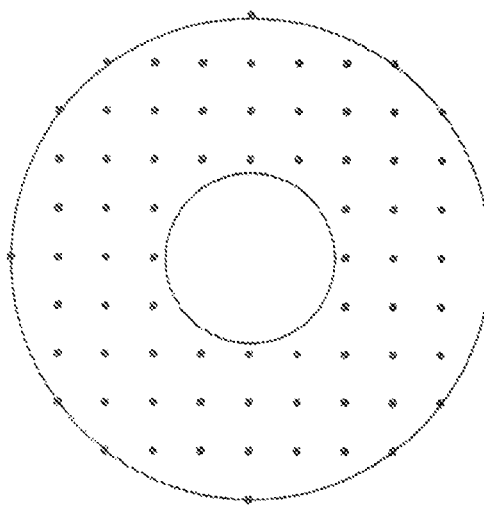
FIGS. 13A to 13E schematically illustrate wavefront sampling points in wavefront reconstruction of various domains, including (A) annular, (B) hexagonal, (C) elliptical, (D) rectangular, and (E) square.
Figure 13B:
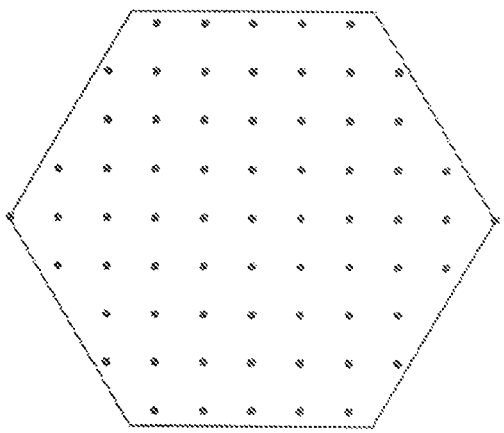
Figure 13C:
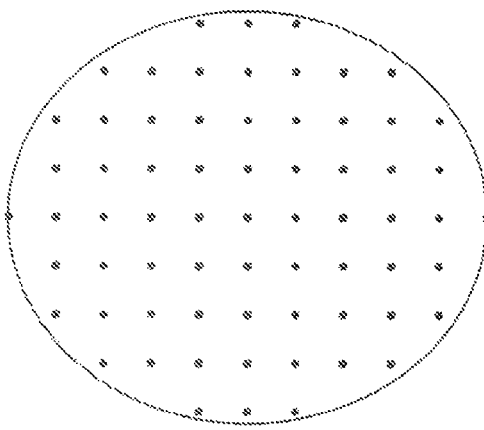
Figure 13D:
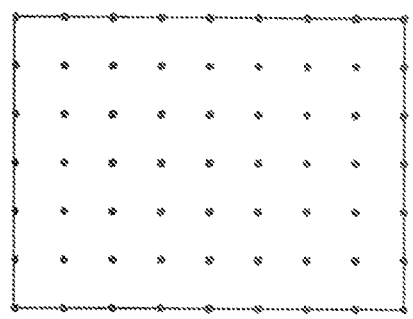
Figure 13E:
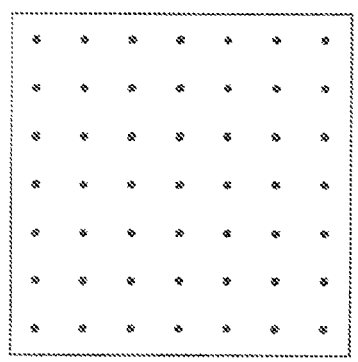

The isometric plots, interferograms, and point-spread functions for the first 4 orders square polynomials $R_1$ through $R_{15}$ are shown in FIG. 11.

Figure 6F:
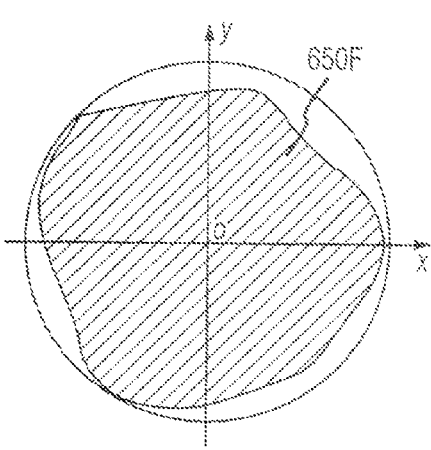
FIG. 6F schematically illustrates an irregular domain and its sub-areas according to embodiments of the present invention.

It should be noted that the Gram-Schmidt orthogonalization process can also be used over irregular pupils, such as one shown in FIG. 6F. The process is similar, except the integration may not be done analytically in some embodiments. In general, it can be performed as summation instead. The same process can also be used over regular or irregular pupils with non-continuous functions, i.e., discrete data. In this case, some or all of the integrations discussed previously can be converted to a summation instead.

2. Dai-Mahajan Technique of Orthonormality

As discussed before, orthonormal polynomials can be calculated from a set of non-orthogonal basis functions by means of the classical Gram-Schmidt orthogonalization process. In some cases, the recursive nature of the process can be slow and laborious. Furthermore, it can be numerically unstable and even lose orthogonality, as pointed out by Å. Björck, *Numerical Methods for Least Square Problems*, SIAM, 1996, the entire contents of which are incorporated herein by reference.

Consider a complete set of polynomials P in an arbitrary coordinate system, e.g., polar coordinates, over an arbitrary domain $\Sigma$. The completeness of P allows any other sets of polynomials to be represented as linear combinations of P, including an orthonormal set F that is orthonormal over domain $\Sigma$. Both sets of polynomials P and F can be one-dimensional, two-dimensional, or multi-dimensional. Therefore, we have $$F_i = \sum_{j=1}^{J} M_{ij} P_j, \tag{23}$$

where $M_{ij}$ is a conversion matrix. If the set of P is known and the conversion matrix M can be determined, the orthonormal polynomials F can be determined. Using the notation of inner products of polynomials, the orthonormality of F can be written as $$\langle F_i | F_j \rangle = \delta_{ij}. \tag{24}$$

In some embodiments it possible to calculate $C^{PP}$ using the inner products of the complete set of polynomials P, for example based on a procedure described in Dai et al. "Non-recursive Determination of Orthonormal Polynomials with Matrix Formulation" Optics Letters 32(1):74-76 (2007), the entire contents of which are incorporated herein by reference for all purposes. This can be done instead of obtaining M directly from the inner product of the complete set of polynomials.

Multiplying $P_{i'}$ on both sides of Eq. (23) and integrating over domain $\Sigma$, we obtain $$\langle P_{i'} | F_i \rangle = \sum_{j=1}^{J} M_{ij} \langle P_{i'} | P_j \rangle \tag{25}$$

$$= \sum_{j=1}^{J} \langle P_{i'} | P_j \rangle M_{ji}$$

Equation (25) can be written in a matrix form as $$C^{PF} = C^{PP} M^T, \tag{26}$$

where $C^{PF}$ is a matrix of inner products between the first N polynomials of P and the first N polynomials of F and $C^{PP}$ is a matrix of inner products of the first N polynomials of P themselves. $M^T$ is the transpose of the conversion matrix M.

Similarly, multiplying $F_{i'}$ on both sides of Eq. (23), integrating over the domain $\Sigma$, and using the orthonormality of F in Eq. (24), we have $$\langle F_{i'} | F_i \rangle = \sum_{j=1}^{J} M_{ij} \langle P_j | F_{i'} \rangle \tag{27}$$

$$= \delta_{ii'}$$

Equation (27) can be written in a matrix form as $$MC^{PF} = 1 \tag{28}$$

Substituting Eq. (26) into Eq. (28), we get $$MC^{PP} M^T = 1. \tag{29}$$

If we let $$M = (Q^T)^{-1}, \tag{30}$$

Eq. (29) can be written as $$Q^T Q = C^{PP}. \tag{31}$$

Because $\langle P_i | P_j \rangle = \langle P_j | P_i \rangle$ and real, matrix $C^{PP}$ is Hermitian. Solution of matrix Q in Eq. (31) can be performed with a standard Cholesky Decomposition, as described in W. H. Press, S. A. Teukolsky, W. Vetterling, and Flannery, *Numerical recipes in C++*, Cambridge University Press, 2002, the full contents of which are incorporated herein by reference. Therefore, the conversion matrix M can be calculated using Eq. (30). As such, the orthonormal polynomials F can be calculated with Eq. (23).

Zernike polynomials and power series can be used as polynomials P because they are complete sets of polynomials. Similarly, Fourier series and Taylor monomials can also be served as polynomials P, since they are also complete. Furthermore, Jacobi polynomials, Chebyshev polynomials, Legendre polynomials, Laguerre polynomials, Hermite polynomials, and the like can also serve as polynomials P. In some embodiments, power series may be preferred because they are simple and they represent naturally in polar coordinates. In the following examples, we will use power series as polynomials P.

As a first example, we derive annular polynomials. As discussed previously, the integration limits are $[1,\epsilon; 0,2\pi]$ in polar coordinates and the area A is $\pi(1-\epsilon^2)$. So the matrix $C^{PP}$ for the first four polynomials is $$C = \begin{bmatrix} 1 & 0 & 0 & \frac{1}{2}(1+\varepsilon^2) \\ 0 & \frac{1}{4}(1+\varepsilon^2) & 0 & 0 \\ 0 & 0 & \frac{1}{4}(1+\varepsilon^2) & 0 \\ \frac{1}{2}(1+\varepsilon^2) & 0 & 0 & \frac{1}{3}(1+\varepsilon^2+\varepsilon^4) \end{bmatrix}, \quad (32a)$$

Solution of Q for the first four polynomials using Eq. (31) is $$Q = \begin{bmatrix} 1 & 0 & 0 & \frac{1}{2}(1+\varepsilon^2) \\ 0 & \frac{\sqrt{1+\varepsilon^2}}{2} & 0 & 0 \\ 0 & 0 & \frac{\sqrt{1+\varepsilon^2}}{2} & 0 \\ 0 & 0 & 0 & \frac{1-\varepsilon^2}{2\sqrt{3}} \end{bmatrix}, \quad (32b)$$

Equation (30) can be used to solve the conversion matrix M for the first four polynomials as $$M = \begin{bmatrix} 1 & 0 & 0 & 0 \\ 0 & \frac{2}{\sqrt{1+\varepsilon^2}} & 0 & 0 \\ 0 & 0 & \frac{2}{\sqrt{1+\varepsilon^2}} & 0 \\ -\frac{\sqrt{3}(1+\varepsilon^2)}{1-\varepsilon^2} & 0 & 0 & \frac{2\sqrt{3}}{1-\varepsilon^2} \end{bmatrix}, \quad (32c)$$

From Eq. (32c), the annular polynomials for the first four terms can be written as $$A_1 = 1 \quad (33)$$
$$A_2 = \frac{2}{\sqrt{1+\varepsilon^2}} \rho\cos\theta$$
$$A_3 = \frac{2}{\sqrt{1+\varepsilon^2}} \rho\sin\theta$$
$$A_4 = \frac{\sqrt{3}}{1-\varepsilon^2}[2\rho^2 - (1+\varepsilon^2)]$$

It should be noted that when $\varepsilon=0$, Eqs. (33) reduce to the corresponding Zernike circle polynomials.

As a second example, we derive hexagonal polynomials. As discussed previously, to do the integration according to some embodiments, we divide the hexagon into three sub-areas, rectangular ACDF 610B, and two similar triangles ABC 620B, and DEF 630B. The x and y integration limits for 610B are $[-\frac{1}{2}, \frac{1}{2}; -\sqrt{3}/2, \sqrt{3}/2]$. Similarly, those for 620B and 630B are $[\frac{1}{2}, 1; -\sqrt{3}(1-x), -\sqrt{3}(1-x)]$ and $[-1, -\frac{1}{2}; -\sqrt{3}(1+x), -\sqrt{3}(1+x)]$, respectively. The area A is $2\sqrt{3}/9$. So the matrix $C^{PP}$ for the first four polynomials is $$C = \begin{bmatrix} 1 & 0 & 0 & \frac{5}{12} \\ 0 & \frac{5}{24} & 0 & 0 \\ 0 & 0 & \frac{5}{24} & 0 \\ \frac{5}{12} & 0 & 0 & \frac{7}{30} \end{bmatrix}, \quad (34a)$$

Solution of Q for the first four polynomials using Eq. (31) is $$Q = \begin{bmatrix} 1 & 0 & 0 & \frac{5}{12} \\ 0 & \frac{1}{2}\sqrt{\frac{5}{6}} & 0 & 0 \\ 0 & 0 & \frac{1}{2}\sqrt{\frac{5}{6}} & 0 \\ 0 & 0 & 0 & \frac{1}{12}\sqrt{\frac{43}{5}} \end{bmatrix}, \quad (34b)$$

Equation (30) can be used to solve the conversion matrix M for the first four polynomials as $$M = \begin{bmatrix} 1 & 0 & 0 & 0 \\ 0 & 2\sqrt{\frac{6}{5}} & 0 & 0 \\ 0 & 0 & 2\sqrt{\frac{6}{5}} & 0 \\ -5\sqrt{\frac{5}{43}} & 0 & 0 & 12\sqrt{\frac{5}{43}} \end{bmatrix}, \quad (34c)$$

From Eq. (34c), the hexagonal polynomials for the first four polynomials can be written as $$H_1 = 1 \quad (35)$$
$$H_2 = 2\sqrt{\frac{6}{5}} \rho\cos\theta$$
$$H_3 = 2\sqrt{\frac{6}{5}} \rho\sin\theta$$
$$H_4 = \sqrt{\frac{5}{43}} (12\rho^2 - 5)$$

As a third example, we derive elliptical polynomials. As discussed previously, the integration limits are $[-\sqrt{e^2-y^2}/e, \sqrt{e^2-y^2}/e; -e, e]$ in Cartesian coordinates. The area A is $\pi e$. So the matrix $C^{PP}$ for the first four terms is $$C = \begin{bmatrix} 1 & 0 & 0 & \frac{1}{4}(1+e^2) \\ 0 & \frac{1}{4} & 0 & 0 \\ 0 & 0 & \frac{e^2}{4} & 0 \\ \frac{1}{4}(1+\varepsilon^2) & 0 & 0 & \frac{1}{24}(3+2e^2+3e^4) \end{bmatrix}, \quad (36a)$$

Solution of Q for the first four terms using Eq. (31) is $$Q = \begin{bmatrix} 1 & 0 & 0 & \frac{1}{4}(1+e^2) \\ 0 & \frac{1}{2} & 0 & 0 \\ 0 & 0 & \frac{e}{2} & 0 \\ 0 & 0 & 0 & \frac{1}{4\sqrt{3}}(3-2e^2+3e^4) \end{bmatrix}, \quad (36b)$$

Equation (30) can be used to solve the conversion matrix M for the first four terms as $$M = \begin{bmatrix} 1 & 0 & 0 & 0 \\ 0 & 2 & 0 & 0 \\ 0 & 0 & \frac{2}{e} & 0 \\ -\frac{\sqrt{3}(1+e^2)}{\sqrt{3-2e^2+3e^4}} & 0 & 0 & \frac{4\sqrt{3}}{\sqrt{3-2e^2+3e^4}} \end{bmatrix}, \quad (36c)$$

From Eq. (36c), the elliptical polynomials for the first four terms can be written as $$E_1 = 1 \quad (37)$$
$$E_2 = 2\rho\cos\theta$$
$$E_3 = \frac{2}{e}\rho\sin\theta$$
$$E_4 = \sqrt{\frac{3}{3-2e^2+3e^4}}[4\rho^2 - (1+e^2)]$$

As a next example, we derive rectangular polynomials. As discussed previously, the integration limits are $[-a, a; -\sqrt{1-a^2}, \sqrt{1-a^2}]$ in Cartesian coordinates. The area A is $4a\sqrt{1-a^2}$. So the matrix $C^{PP}$ for the first four polynomials is $$C = \begin{bmatrix} 1 & 0 & 0 & \frac{1}{3} \\ 0 & \frac{a^2}{3} & 0 & 0 \\ 0 & 0 & \frac{1}{3}(1-a^2) & 0 \\ \frac{1}{3} & 0 & 0 & \frac{1}{45}(9-8a^2+8a^4) \end{bmatrix}, \quad (38a)$$

Solution of Q for the first four polynomials using Eq. (31) is $$Q = \begin{bmatrix} 1 & 0 & 0 & \frac{1}{3} \\ 0 & \frac{a}{\sqrt{3}} & 0 & 0 \\ 0 & 0 & \sqrt{\frac{1-a^2}{3}} & 0 \\ 0 & 0 & 0 & \frac{2}{3}\sqrt{\frac{1-2a^2+2a^4}{5}} \end{bmatrix}, \quad (38b)$$

Equation (30) can be used to solve the conversion matrix M for the first four polynomials as $$M = \begin{bmatrix} 1 & 0 & 0 & 0 \\ 0 & \frac{\sqrt{3}}{a} & 0 & 0 \\ 0 & 0 & \sqrt{\frac{3}{1-a^2}} & 0 \\ -\frac{\sqrt{5}}{2\sqrt{1-2a^2+2a^4}} & 0 & 0 & \frac{3\sqrt{5}}{2\sqrt{1-2a^2+2a^4}} \end{bmatrix}, \quad (38c)$$

From Eq. (38c), the first four rectangular polynomials can be written as $$R_1 = 1 \quad (39)$$
$$R_2 = \frac{\sqrt{3}}{a}\rho\cos\theta$$
$$R_3 = \sqrt{\frac{3}{1-a^2}}\rho\sin\theta$$
$$R_4 = \frac{1}{2}\sqrt{\frac{5}{1-2a^2+2a^4}}(3\rho^2-1)$$

As a final example, we derive square polynomials. As discussed previously, the integration limits are $[-1/\sqrt{2}, 1/\sqrt{2}; -1/\sqrt{2}, 1/\sqrt{2}]$ in Cartesian coordinates. The area A is 2. So the matrix $C^{PP}$ for the first four polynomials is $$C = \begin{bmatrix} 1 & 0 & 0 & \frac{1}{3} \\ 0 & \frac{1}{6} & 0 & 0 \\ 0 & 0 & \frac{1}{6} & 0 \\ \frac{1}{3} & 0 & 0 & \frac{7}{45} \end{bmatrix}, \quad (40a)$$

Solution of Q for the first four polynomials using Eq. (31) is $$Q = \begin{bmatrix} 1 & 0 & 0 & \frac{1}{3} \\ 0 & \frac{1}{\sqrt{6}} & 0 & 0 \\ 0 & 0 & \frac{1}{\sqrt{6}} & 0 \\ 0 & 0 & 0 & \frac{1}{3}\sqrt{\frac{2}{5}} \end{bmatrix}, \quad (40b)$$

Equation (30) can be used to solve the conversion matrix M for the first four polynomials as $$M = \begin{bmatrix} 1 & 0 & 0 & 0 \\ 0 & \sqrt{6} & 0 & 0 \\ 0 & 0 & \sqrt{6} & 0 \\ -\sqrt{\frac{2}{5}} & 0 & 0 & 3\sqrt{\frac{2}{5}} \end{bmatrix}, \quad (40c)$$

From Eq. (40c), the square polynomials for the first four terms can be written as $$S_1 = 1 \quad (41)$$
$$S_2 = \sqrt{6}\,\rho\cos\theta$$
$$S_3 = \sqrt{6}\,\rho\sin\theta$$
$$S_4 = \sqrt{\frac{5}{2}}(3\rho^2 - 1)$$

They can also be obtained from the rectangular polynomials by letting $a \to 1/\sqrt{2}$.

When the pupil is not regular, as the one shown in FIG. 6F, analytical solution of matrix C, Q, and M may not be possible. However, it is possible to do it numerically. For example, the inner product of power series over irregular pupil can be written as $$\langle P_i | P_j \rangle = \frac{1}{N}\sum_{l=1}^{N} P_i(\rho_l, \theta_l) P_j(\rho_l, \theta_l), \quad (42)$$

where N is the total number of discrete data points within the irregular pupil. With Eq. (42), matrix $C^{PP}$ can be calculated. Therefore, Q and M matrices can also be calculated, all numerically.

C. Error Analysis

Zernike polynomials are commonly used in optical design and testing. Their use is proper when the pupil is circular. However, when the pupil is noncircular, their use may imply error. For any orthonormal polynomials F, suppose we use them to represent a wavefront $W(\rho, \theta)$ as $$W(\rho, \theta) = \sum_{i=1}^{J} c_i F_i(\rho, \theta), \quad (43)$$

where the expansion coefficient $c_j$ and be calculated from the orthonormality of F as $$c_j = \frac{1}{A}\int_\Sigma W(\rho, \theta) F_j(\rho, \theta) d^2\rho = \langle W | F_j \rangle. \quad (44)$$

The average of the wavefront can be calculated as $$\overline{W}(\rho, \theta) = \frac{1}{A}\int_\Sigma W(\rho, \theta) d^2\rho = \langle W | F_1 \rangle. \quad (45)$$

Comparison of Eqs. (44) and (45), we get, $$\overline{W} = c_1 \quad (46)$$

Equation (46) indicates that the mean value of a wavefront within the domain $\Sigma$ equals the piston coefficient of the orthonormal polynomials. The variance of the wavefront can be expressed as $$\sigma^2 = \frac{1}{A}\int_\Sigma |W - \overline{W}|^2 d^2\rho \quad (47)$$
$$= \frac{1}{A}\int_\Sigma \left|\sum_{i=1}^{J} c_i F_i - c_1\right|^2 d^2\rho$$
$$= \sum_{i=2}^{J}\sum_{i'=2}^{J} c_i c_{i'} \frac{1}{A}\int_\Sigma F_i F_{i'} d^2\rho$$
$$= \sum_{i=2}^{J}\sum_{i'=2}^{J} c_i c_{i'} \delta_{ii'}$$
$$= \sum_{i=2}^{J} c_i^2$$

Equation (47) indicates that the variance of a wavefront within the domain $\Sigma$ equals the sum of the square of the coefficients of the orthonormal polynomials, excluding the piston coefficient. Because of this property, the orthonormal polynomials may be preferred than any non-orthogonal polynomials.

If we use Zernike circle polynomials instead of the orthonormal polynomials, we can express the wavefront as $$\hat{W}(\rho, \theta) = \sum_{j=1}^{J} a_j Z_j(\rho, \theta). \quad (48)$$

From Eqs. (43) and (48), we obtain the error when we use Eq. (48) as $$\Delta = \frac{1}{A}\int_\Sigma |W - \hat{W}|^2 d^2\rho \quad (49)$$

Substituting Eqs. (43) and (48) into (49) and some laborious arithmetic, we obtain $$\Delta = \sum_{j=1}^{J} c_j^2 + \sum_{j=1}^{J} a_j \sum_{j'=1}^{J} \langle Z_j | Z_{j'} \rangle a_{j'} - 2 \sum_{j=1}^{J} a_j \sum_{j'=1}^{J} \langle Z_j | F_{j'} \rangle c_{j'} \quad (50)$$

Equation (50) can be written in a matrix form as $$\Delta = A^T A - 2B^T C^{ZF} A + B^T C^{ZZ} B, \quad (51)$$

where A stands for a column vector containing the $c_j$ coefficients and B denotes a column vector containing the $a_j$ coefficients. Matrices $C^{ZZ}$ and $C^{ZF}$ are similar to the matrix $C^{PP}$ mentioned previously.

To derive the relationship between the F-polynomials coefficients $c_i$ and the Zernike coefficients $a_j$, we begin by considering the situation where a wavefront map is known and to be fitted with Zernike circle polynomials within the domain Σ. From a least square point of view, one way to use Zernike polynomials is to make $\hat{W}=W$. Hence from Eqs. (43) and (48), we have $$\sum_{j=1}^{J} a_j Z_j = \sum_{j=1}^{J} c_j F_j \quad (52)$$

Multiplying $Z_{j'}$ on both sides of Eq. (52) and integrating over the domain Σ, we get $$\sum_{j=1}^{J} a_j \langle Z_{j'} | Z_j \rangle = \sum_{j=1}^{J} c_j \langle Z_{j'} | F_j \rangle \quad (53)$$

Equation (53) can be written in a matrix form as $$C^{ZZ} B = C^{ZF} A. \quad (54)$$

When the domain Σ is a circular pupil, F-polynomials becomes Zernike circle polynomials and therefore, B=A. For noncircular pupils, solution of B from Eq. (54) can be done with a matrix inversion as $$B = [C^{ZZ}]^{-1} C^{ZF} A. \quad (55)$$

Because the matrix $C^{ZZ}$ is well behaved, its inverse can be determined analytically. Equation (55) is the correct way of calculating the Zernike coefficients when the pupil is noncircular. It results in no wavefront fitting error.

However, because we may not have the orthonormal polynomials, A may be unknown and Eq. (55) may be unusable in practice. When Zernike circle polynomials are used, perhaps incorrectly, over noncircular pupil, we have $$a_j = \frac{1}{A} \int_{\Sigma} W(\rho, \theta) Z_j(\rho, \theta) d^2 \rho \quad (56)$$

$$= \sum_{j'=1}^{J} c_{j'} \frac{1}{A} \int_{\Sigma} Z_j(\rho, \theta) F_{j'}(\rho, \theta) d^2 \rho$$

$$= \sum_{j'=1}^{J} c_{j'} \langle Z_j | F_{j'} \rangle.$$

Equation (56) can be written in a matrix form as $$B = C^{ZF} A. \quad (57)$$

Substituting Eq. (57) into Eq. (51) yields $$\Delta = A^T (1-P) A, \quad (58)$$

where $$P = (C^{ZF})^T (2 - C^{ZZ}) C^{ZF}. \quad (59)$$

Matrix P is termed the deviation matrix of wavefront fitting. It indicates how much it is different from the unitary matrix 1. When the domain Σ is a circular pupil, F=Z so matrix P is 1, because both matrices $C^{ZZ}$ and $C^{ZF}$ are 1. In this case, Δ=0 so there is no fitting error by using Zernike circle polynomials. However, when the domain Σ is noncircular, Δ will not be zero.

In wavefront fitting, improper calculation of Zernike coefficients can result in error in the fitted wavefront. FIG. 12A shows the fitting error of the wavefront when each of the individual terms is used for hexagonal and square pupils. For example, if the wavefront to be fitted contains only one wave of the balanced defocus, the fitting error with the use of Zernike circle polynomials will be 0.158 wave for the hexagonal pupil and 0.324 wave for the square pupil, representing a 16% and a 32% error, respectively, according to some embodiments.

FIG. 12A also indicates that for hexagonal pupils, use of Zernike circle polynomials can result in the least error for $H_{10}$ but the greatest error for $H_{11}$, according to some embodiments. Similar, for square pupils, $S_6$ results in the least error and $S_{12}$ results in the greatest error, according to some embodiments.

For annular pupils, the fitting error is negligible when ϵ<0.2, as can be seen in FIGS. 12B(i) and 12B(ii). At ϵ=0.2, the greatest error comes from $A_{11}$, which is less than 5%. This explains it is rather safe to use Zernike circle polynomials as basis functions for astronomical applications. However, as & increases, the fitting error for terms with m=n, such as $A_2$, $A_3$, $A_5$, $A_6$, $A_9$, $A_{10}$, $A_{11}$, and $A_{15}$, the fitting error can be as much as 50 times the input wavefront error.

FIGS. 12C(i) to 12C(iii) show the fitting error as a function of the aspect ratio α for elliptical pupils, which is very different from the fitting error for annular pupils. The least error for elliptical pupils occurs for $E_6$, $E_{10}$, and $E_{14}$, where m=n.

For rectangular pupils, the fitting error as a function of the aspect ratio a is shown in FIGS. 12D(i) to 12D(iii). Again, the error in this case is very different from that for annular and elliptical pupils. The least error for many terms occurs when 0.5≤a≤0.9, but the greatest for other terms.

Consider the case where the wavefront is reconstructed from slope-type data using modal reconstruction approach. Taking derivatives with respective to x and toy of both sides of Eq. (43) for each of the k data points (l=1, 2, . . . , k) yields $$\left.\frac{\partial W}{\partial x}\right|_l = \sum_{j=1}^{J} c_i \left.\frac{\partial F_j}{\partial x}\right|_l \quad (60)$$

$$\left.\frac{\partial W}{\partial y}\right|_l = \sum_{j=1}^{J} c_i \left.\frac{\partial F_j}{\partial x}\right|_l$$

Equation (60) applied to all k data points can be written as a matrix form as $$S = GA, \quad (61)$$

where S is an array of the x- and y-slope data, A is an array of coefficients and G is a matrix of the derivatives of the F-polynomials at the measurement points and can be written as $$G = \begin{pmatrix} \frac{\partial F_1(x,y)_1}{\partial x} & \frac{\partial F_2(x,y)_1}{\partial x} & \cdots & \frac{\partial F_N(x,y)_1}{\partial x} \\ \frac{\partial F_1(x,y)_1}{\partial y} & \frac{\partial F_2(x,y)_1}{\partial y} & \cdots & \frac{\partial F_N(x,y)_1}{\partial y} \\ \vdots & \vdots & \ddots & \vdots \\ \frac{\partial F_1(x,y)_k}{\partial x} & \frac{\partial F_2(x,y)_k}{\partial x} & \cdots & \frac{\partial F_N(x,y)_k}{\partial x} \\ \frac{\partial F_1(x,y)_k}{\partial y} & \frac{\partial F_2(x,y)_k}{\partial y} & \cdots & \frac{\partial F_N(x,y)_k}{\partial y} \end{pmatrix}. \quad (62)$$

Similarly, taking derivatives with respect to x and y of both sides of Eq. (48) for each of the k data points (l=1, 2, ..., k) yields $$\left.\frac{\partial \hat{W}}{\partial x}\right|_l = \sum_{j=1}^{J} a_j \left.\frac{\partial Z_j}{\partial x}\right|_l \quad (63)$$

$$\left.\frac{\partial \hat{W}}{\partial y}\right|_l = \sum_{j=1}^{J} a_j \left.\frac{\partial Z_j}{\partial x}\right|_l$$

Equation (63) can be written as a matrix form as $$\hat{S} = HB, \quad (64)$$

where $\hat{S}$ is an array of estimated x- and y-slope data, B is an array of coefficients and H is a matrix of Z-derivatives at the measurement points and can be written as $$H = \begin{pmatrix} \frac{\partial Z_1(x,y)_1}{\partial x} & \frac{\partial Z_2(x,y)_1}{\partial x} & \cdots & \frac{\partial Z_N(x,y)_1}{\partial x} \\ \frac{\partial Z_1(x,y)_1}{\partial y} & \frac{\partial Z_2(x,y)_1}{\partial y} & \cdots & \frac{\partial Z_N(x,y)_1}{\partial y} \\ \vdots & \vdots & \ddots & \vdots \\ \frac{\partial Z_1(x,y)_k}{\partial x} & \frac{\partial Z_2(x,y)_k}{\partial x} & \cdots & \frac{\partial Z_N(x,y)_k}{\partial x} \\ \frac{\partial Z_1(x,y)_k}{\partial y} & \frac{\partial Z_2(x,y)_k}{\partial y} & \cdots & \frac{\partial Z_N(x,y)_k}{\partial y} \end{pmatrix}. \quad (65)$$

To calculate the matrix H, it is helpful to know the derivatives of the Zernike circle polynomials. The least squares solution of Eq. (65) is $$B = (H^T H)^{-1} H^T S = H^+ S, \quad (66)$$

where $H^T$ denotes the transpose of matrix H and $H^+$ is the generalized inverse of matrix H.

Substituting Eq. (66) into Eq. (51), we get $$\Delta = A^T (1-Q) A, \quad (67)$$

where the matrix Q is $$Q = (H^+ G)^T (2 C^{ZF} - C^{ZZ} H^+ G). \quad (68)$$

Similar to matrix P, matrix Q is termed the deviation matrix of wavefront reconstruction. It indicates how much it is different from the unitary matrix 1. When the domain Σ is a circular area, F=Z so matrix Q=1, because both matrixes $C^{ZZ}$ and $C^{ZF}$ as well as $H^+G$ are 1. In this case Δ=0 so there is no additional reconstruction error by using the Zernike circle polynomials. However, when domain Σ is non-circular, there can be an additional error due to use Zernike circle polynomials for wavefront reconstruction.

To investigate the wavefront reconstruction error, we can assume some specific configurations of data sampling points over which wavefront slopes are given. FIGS. 13A to 13E show the configurations for annular, hexagonal, elliptical, rectangular, and square pupils, respectively. In these configurations, 11×11 evenly sampled points over a square area that inscribes the unit circle are shown. Also investigated, are configurations with 41×41 and 101×101 sampling points.

FIGS. 14A and 14B show the reconstruction error for hexagonal and square pupils, respectively, according to some embodiments. In both cases, the wavefront tilts ($H_2$, $H_2$, $S_2$ and $S_3$) can have the least error. This may be because the balanced tilts represent wavefront slopes, which become a constant in the slope data. The greatest error comes from the balanced defocus ($H_4$ and $S_4$), according to some embodiments. In addition, balanced astigmatism ($H_5$, $H_6$, $S_5$ and $S_6$) can also show relatively small error. Furthermore, change of the sampling ratio by four folds may not change the reconstruction error by much. Therefore, in the other three pupil shapes, we only consider sampling configurations of 101×101, according to some embodiments.

For annular pupils, the reconstruction error as a function of ε is shown in FIGS. 14C(i) and 14C(ii) for 101×101 configuration. Again, error for some terms shows monotonical changes as a function of ε, but that for other terms fluctuates severely.

FIGS. 14D(i) to 14D(iii) show the reconstruction error as a function of the aspect ratio a for configurations 101×101, according to some embodiments. For most terms, the reconstruction error increases as a decreases, although the increase of the error for $E_{11}$ and $E_{12}$ is not monotonical. It is also clear that $E_3$, $E_8$ and $E_{12}$ have relatively smaller error and $E_6$, $E_7$ and $E_{13}$ have relatively greater error, according to some embodiments.

For rectangular pupils, $R_4$ and $R_{12}$ show the greatest reconstruction error as compared to other terms, as can be seen in FIGS. 14E(i) to 14E(iii), representing configurations of 101×101.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

A variety of modifications are possible within the scope of the present invention. For example, a complete set of polynomials may be changed to Fourier series or Taylor monomials. Furthermore, other complete sets of polynomials, such as Jacobi polynomials, Chebyshev polynomials, Legendre polynomials, Laguerre polynomials, and Hermite polynomials, can also be used. A variety of domains can be considered in the determination of orthonormal polynomials. These domains can be one-dimensional, two-dimensional, or multi-dimensional. Within two-dimensional domains, a variety of pupil shapes, such as circular, annular, hexagonal, elliptical, rectangular, square, and irregular can be used. While the specific embodiments have been described in some detail, by way of example and for clarity of understanding, a variety of adaptations, changes, and modifications will be obvious to those of skill in the art. Although the invention has been described with specific reference to optical testing and design, other suitable applications in fields such as physics, engineering, mathematics, applied mathematics, and the like can find applications for the determination of orthonormal polynomials from a set of simple, non-orthogonal polynomials. Therefore, the scope of the present invention is limited solely by the specific claims.

What is claimed is:

1. A method of determining a vision treatment for a patient based on a set of orthonormal polynomials F over a domain $\Sigma$ corresponding to a pupil of an eye of the patient, the method comprising:

using a processing hardware having a non-transitory tangible medium embodying machine-readable code associated therewith to determine the vision treatment for the patient based on the set of orthonormal polynomials F, the vision treatment comprising a spectacle lens shape, an intraocular lens shape, a contact lens shape, a corneal ring implant shape, a corneal inlay shape, a corneal onlay shape, a corneal implant shape, or a laser treatment shape, wherein the domain $\Sigma$ has a shape selected from the group consisting of a hexagon, an ellipse, an annulus, a rectangle, and a square, such that:

when the domain $\Sigma$ has the hexagon shape, the set of orthonormal polynomials F includes a polynomial term of 1, a polynomial term of $$2\sqrt{\frac{6}{5}}\rho\cos\theta,$$

a polynomial term of $$2\sqrt{\frac{6}{5}}\rho\sin\theta,$$

and polynomial term of $$\sqrt{\frac{5}{43}}(12\rho^2 - 5),$$

when the domain $\Sigma$ has the ellipse shape, the set of orthonormal polynomials F includes a polynomial term of 1, a polynomial term of $2\rho\cos\theta$, a polynomial term of $$\frac{2}{e}\rho\sin\theta,$$

and polynomial term of $$\sqrt{\frac{3}{3 - 3e^2 + 3e^4}}[4\rho^2 - (1 + e^2)],$$

when the domain $\Sigma$ has the annulus shape, the set of orthonormal polynomials F includes a polynomial term of 1, a polynomial term of $$\frac{2}{\sqrt{1+\varepsilon^2}}2\rho\cos\theta,$$

a polynomial term of $$\frac{2}{\sqrt{1+\varepsilon^2}}2\rho\sin\theta,$$

and polynomial term of $$\frac{\sqrt{3}}{1-\varepsilon^2}[2\rho^2 - (1+e^2)],$$

when the domain $\Sigma$ has the rectangle shape, the set of orthonormal polynomials F includes a polynomial term of 1, a polynomial term of $$\frac{\sqrt{3}}{a}\rho\cos\theta,$$

a polynomial term of $$\sqrt{\frac{3}{1-a^2}}\rho\sin\theta,$$

and polynomial term of $$\frac{1}{2}\sqrt{\frac{5}{1 - 2a^2 + 2a^4}}(3\rho^2 - 1),$$

and
when the domain $\Sigma$ has the square shape, the set of orthonormal polynomials F includes a polynomial term of 1, a polynomial term of $\sqrt{6}\rho\cos\theta$, a polynomial term of $\sqrt{6}\rho\sin\theta$, and polynomial term of $$\sqrt{\frac{5}{2}}(3\rho^2 - 1),$$

wherein $\rho$ and $\theta$ are polar coordinates,
wherein e and a are aspect ratios, and
wherein $\epsilon$ is an obscuration ratio.

2. The method according to claim 1, wherein the domain $\Sigma$ has the hexagon shape.

3. The method according to claim 1, wherein the domain $\Sigma$ has the ellipse shape.

4. The method according to claim 1, wherein the domain $\Sigma$ has the annulus shape.

5. The method according to claim 1, wherein the domain $\Sigma$ has the rectangle shape.

6. The method according to claim 1, wherein the domain $\Sigma$ has the square shape.

7. A system for determining a vision treatment for a patient based on a set of orthonormal polynomials F over a domain $\Sigma$ corresponding to a pupil of an eye of the patient, the system comprising:
a processor; and
a treatment module comprising a non-transitory tangible medium embodying machine readable code that, when executed on the processor, is configured to cause the system to determine the vision treatment for the patient based on the set of orthonormal polynomials F,
wherein the domain $\Sigma$ has a shape selected from the group consisting of a hexagon, an ellipse, an annulus, a rectangle, and a square, such that:
when the domain $\Sigma$ has the hexagon shape, the set of orthonormal polynomials F includes a polynomial term of 1, a polynomial term of $$2\sqrt{\frac{6}{5}}\rho\cos\theta,$$

a polynomial term of $$2\sqrt{\frac{6}{5}}\rho\sin\theta,$$

and polynomial term of $$\sqrt{\frac{5}{43}}(12\rho^2 - 5),$$

when the domain $\Sigma$ has the ellipse shape, the set of orthonormal polynomials F includes a polynomial term of 1, a polynomial term of $2\rho\cos\theta$, a polynomial term of $$\frac{2}{e}\rho\sin\theta,$$

and polynomial term of $$\sqrt{\frac{3}{3 - 2e^2 + 3e^4}}[4\rho^2 - (1 + e^2)],$$

when the domain $\Sigma$ has the annulus shape, the set of orthonormal polynomials F includes a polynomial term of 1, a polynomial term of $$\frac{2}{\sqrt{1+\varepsilon^2}}2\rho\cos\theta,$$

a polynomial term of $$\frac{2}{\sqrt{1+\varepsilon^2}}2\rho\sin\theta,$$

and polynomial term of $$\frac{\sqrt{3}}{1-\varepsilon^2}[2\rho^2 - (1 + e^2)],$$

when the domain $\Sigma$ has the rectangle shape, the set of orthonormal polynomials F includes a polynomial term of 1, a polynomial term of $$\frac{\sqrt{3}}{a}\rho\cos\theta,$$

a polynomial term of $$\sqrt{\frac{3}{1-a^2}}\rho\sin\theta,$$

and polynomial term of $$\frac{1}{2}\sqrt{\frac{5}{1-2a^2+2a^4}}(3\rho^2 - 1),$$

and
when the domain $\Sigma$ has the square shape, the set of orthonormal polynomials F includes a polynomial term of 1, a polynomial term of $\sqrt{6}\rho\cos\theta$, a polynomial term of $\sqrt{6}\rho\sin\theta$, and polynomial term of $$\sqrt{\frac{5}{2}}(3\rho^2 - 1),$$

wherein $\rho$ and $\theta$ are polar coordinates,
wherein e and a are aspect ratios, and
wherein $\epsilon$ is an obscuration ratio.

8. The system according to claim 7, wherein the domain $\Sigma$ has the hexagon shape.

9. The system according to claim 7, wherein the domain $\Sigma$ has the ellipse shape.

10. The system according to claim 7, wherein the domain $\Sigma$ has the annulus shape.

11. The system according to claim 7, wherein the domain $\Sigma$ has the rectangle shape.

12. The system according to claim 7, wherein the domain $\Sigma$ has the square shape.

13. The system according to claim 7, wherein the vision treatment comprises a member selected from the group consisting of a spectacle lens shape, an intraocular lens shape, a contact lens shape, a corneal ring implant shape, a corneal inlay shape, a corneal onlay shape, a corneal implant shape, or a laser treatment shape.

14. A method of determining a vision treatment for a patient based on a set of orthonormal polynomials F over a domain $\Sigma$ corresponding to a pupil of an eye of the patient, the method comprising:
   using a processing hardware having a non-transitory tangible medium embodying machine-readable code associated therewith to determine the vision treatment for the patient based on the set of orthonormal polynomials F,
   wherein the domain $\Sigma$ has a noncircular shape,
   wherein the set of orthonormal polynomials F includes a polynomial term of 1, a polynomial term that is a factor of $\rho \cos \theta$, and a polynomial term that is a factor of $\rho \sin \theta$, and a polynomial term that includes $\rho^2$, and
   wherein $\rho$ and $\theta$ are polar coordinates.

15. The method according to claim 14, wherein the domain $\Sigma$ has a shape selected from the group consisting of a hexagon, an ellipse, an annulus, a rectangle, a square, and an irregular shape.

16. The method according to claim 14, wherein the domain $\Sigma$ has an irregular shape.

17. The method according to claim 14, wherein the vision treatment comprises a member selected from the group consisting of a spectacle lens shape, an intraocular lens shape, a contact lens shape, a corneal ring implant shape, a corneal inlay shape, a corneal onlay shape, a corneal implant shape, or a laser treatment shape.

18. A system for determining a vision treatment for a patient based on a set of orthonormal polynomials F over a domain $\Sigma$ corresponding to a pupil of an eye of the patient, the system comprising:
   a processor; and
   a treatment module comprising a non-transitory tangible medium embodying machine readable code that, when executed on the processor, is configured to cause the system to determine the vision treatment for the patient based on the set of orthonormal polynomials F,
   wherein the domain $\Sigma$ has a noncircular shape,
   wherein the set of orthonormal polynomials F includes a polynomial term of 1, a polynomial term that is a factor of $\rho \cos \theta$, and a polynomial term that is a factor of $\rho \sin \theta$, and a polynomial term that includes $\rho^2$, and
   wherein $\rho$ and $\theta$ are polar coordinates.

19. The system according to claim 18, wherein the domain $\Sigma$ has a shape selected from the group consisting of a hexagon, an ellipse, an annulus, a rectangle, a square, and an irregular shape.

20. The system according to claim 18, wherein the domain $\Sigma$ has an irregular shape.

21. The system according to claim 18, wherein the vision treatment comprises a member selected from the group consisting of a spectacle lens shape, an intraocular lens shape, a contact lens shape, a corneal ring implant shape, a corneal inlay shape, a corneal onlay shape, a corneal implant shape, or a laser treatment shape.

* * * * *

UNITED STATES PATENT AND TRADEMARK OFFICE
CERTIFICATE OF CORRECTION

| | | |
|---|---|---|
| PATENT NO. | : 8,983,812 B2 | Page 1 of 1 |
| APPLICATION NO. | : 13/871143 | |
| DATED | : March 17, 2015 | |
| INVENTOR(S) | : Guang-Ming Dai and Virendra N. Mahajan | |

It is certified that error appears in the above-identified patent and that said Letters Patent is hereby corrected as shown below:

On the Title page:
  Item (71), please replace "Clara" with --Ana--.

In the Claims:
  Column 30, line 10, please replace "$3e^2$" with --$2e^2$--.

Signed and Sealed this
Eleventh Day of August, 2015

Michelle K. Lee
*Director of the United States Patent and Trademark Office*